(12) United States Patent
Smith et al.

(10) Patent No.: US 10,692,892 B2
(45) Date of Patent: Jun. 23, 2020

(54) METHOD OF PROVIDING AN IMAGING SYSTEM AND IMAGING SYSTEM THEREOF

(71) Applicants: Joseph Smith, Tempe, AZ (US); Rita Bottesch, Mesa, AZ (US); John Stowell, Tempe, AZ (US)

(72) Inventors: Joseph Smith, Tempe, AZ (US); Rita Bottesch, Mesa, AZ (US); John Stowell, Tempe, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

(21) Appl. No.: 16/601,411

(22) Filed: Oct. 14, 2019

(65) Prior Publication Data

US 2020/0043952 A1   Feb. 6, 2020

Related U.S. Application Data

(60) Division of application No. 15/334,143, filed on Oct. 25, 2016, now Pat. No. 10,446,582, which is a
(Continued)

(51) Int. Cl.
| | |
|---|---|
| H01L 27/12 | (2006.01) |
| H01L 23/498 | (2006.01) |
| H01L 21/683 | (2006.01) |
| H01L 23/31 | (2006.01) |
| H01L 21/768 | (2006.01) |
| H01L 27/146 | (2006.01) |

(Continued)

(52) U.S. Cl.
CPC ........ *H01L 27/1218* (2013.01); *G01T 1/2018* (2013.01); *H01L 21/30604* (2013.01); *H01L 21/6835* (2013.01); *H01L 21/768* (2013.01); *H01L 23/3192* (2013.01); *H01L 23/4985* (2013.01); *H01L 27/1262* (2013.01); *H01L 27/14636* (2013.01); *H01L 27/14663* (2013.01); *H01L 27/153* (2013.01); *H01L 29/78603* (2013.01); *A61B 2562/02* (2013.01); *A61B 2562/164* (2013.01); *H01L 23/15* (2013.01); *H01L 27/14603* (2013.01); *H01L 33/0079* (2013.01); *H01L 2221/6835* (2013.01); *H01L 2221/68381* (2013.01); *H01L 2924/00* (2013.01); *H01L 2924/0002* (2013.01)

(58) Field of Classification Search
None
See application file for complete search history.

*Primary Examiner* — Nilufa Rahim
(74) *Attorney, Agent, or Firm* — Bryan Cave Leighton Paisner LLP

(57) ABSTRACT

Some embodiments include an imaging system. The imaging system can comprise: a scintillator structure; and an electronic device engaged with the scintillator structure, wherein: the scintillator structure can comprise: a scintillator support layer; and a scintillator layer; the scintillator support layer can comprise: a first substantially non-planar surface; and a second substantially non-planar surface, the first substantially non-planar surface can be approximately parallel to the second substantially non-planar surface; the electronic device can comprise a device substrate and one or more active sections; the device substrate can comprise a first surface and a second surface opposite the first surface of the device substrate; the one or more active sections are at the second surface of the device substrate; and the second surface of the device substrate and the one or more active sections can conform to the second surface of the scintillator layer. Other embodiments are described herein.

20 Claims, 22 Drawing Sheets

Related U.S. Application Data continuation-in-part of application No. 14/979,087, filed on Dec. 22, 2015, now Pat. No. 9,741,742, and a continuation-in-part of application No. 15/006,935, filed on Jan. 26, 2016, now abandoned, which is a continuation of application No. 14/979,087, filed on Dec. 22, 2015, now Pat. No. 9,741,742.

(60) Provisional application No. 62/246,451, filed on Oct. 26, 2015, provisional application No. 62/115,233, filed on Feb. 12, 2015, provisional application No. 62/095,579, filed on Dec. 22, 2014.

(51) Int. Cl.
| | |
|---|---|
| *H01L 27/15* | (2006.01) |
| *H01L 21/306* | (2006.01) |
| *G01T 1/20* | (2006.01) |
| *H01L 29/786* | (2006.01) |
| *H01L 33/00* | (2010.01) |
| *H01L 23/15* | (2006.01) |

METHOD OF PROVIDING AN IMAGING SYSTEM AND IMAGING SYSTEM THEREOF

CROSS-REFERENCE TO RELATED APPLICATIONS

This application is a divisional of U.S. patent application Ser. No. 15/334,143, filed Oct. 25, 2016. U.S. patent application Ser. No. 15/334,143 in turn claims the benefit of U.S. Provisional Patent Application No. 62/246,451, filed Oct. 26, 2015.

Further, U.S. patent application Ser. No. 15/334,143 is a continuation-in-part of U.S. Non-Provisional patent application Ser. No. 14/979,087, filed Dec. 22, 2015, and U.S. Non-Provisional patent application Ser. No. 15/006,935, filed Jan. 26, 2016.

In addition, U.S. Non-Provisional patent application Ser. No. 14/979,087 claims the benefit of U.S. Provisional Patent Application No. 62/095,579, filed Dec. 22, 2014, and claims the benefit of U.S. Provisional Patent Application No. 62/115,233, filed Feb. 12, 2015.

Meanwhile, U.S. Non-Provisional patent application Ser. No. 15/006,935 is a continuation of U.S. Non-Provisional patent application Ser. No. 14/979,087 and claims the benefit of U.S. Provisional Patent Application No. 62/115,233.

U.S. patent application Ser. No. 15/334,143, U.S. Provisional Patent Application No. 62/246,451, U.S. Non-Provisional patent application Ser. No. 14/979,087, U.S. Non-Provisional patent application Ser. No. 15/006,935, U.S. Provisional Patent Application No. 62/095,579, and U.S. Provisional Patent Application No. 62/115,233 are incorporated herein by reference in their entirety.

STATEMENT REGARDING FEDERALLY SPONSORED RESEARCH OR DEVELOPMENT

This invention was made with government support under W911NF-04-2-0005 awarded by the Army Research Office. The government has certain rights in the invention.

FIELD OF THE INVENTION

This invention relates generally to imaging systems, and relates more particularly to three dimensional (3D) conformal imaging systems and methods of providing and using the same.

BACKGROUND OF THE INVENTION

Deformable (e.g., flexible and/or stretchable) device substrates, which can include a wide variety of materials, such as, for example, any of a myriad of plastics, metal foils, and glasses, are quickly becoming popular as bases for electronic devices. For example, a deformable device substrate can provide an advantageous base for a wearable consumer electronic device, a flat panel display, an active matrix array of an imaging system, etc.

Generally, the physical architecture of an imaging system can limit the usability of the imaging system. For example, an imaging system implementing a rigid and/or a two dimensional (2D) active matrix array may be unsuitable for imaging certain objects with sufficient quality, and in some cases, may be unable to image such objects at all. For example, it may not be possible to position an imagining system with a 2D active matrix array close enough to an object to image the object with sufficient quality. Meanwhile, it may not be possible to image an object using an imaging system with a rigid active matrix array because the imaging system may not fit in the space adjacent to the object. For example, the space may be a confined volume, such as, for example, the internal volume of a conduit.

In order to overcome the architectural limitations of imaging systems implementing rigid and/or 2D active matrix arrays, 3D conformal imaging systems are needed. Deformable (e.g., flexible and/or stretchable) device substrates can help to provide 3D conformal imaging systems by allowing for deformable active matrix arrays, but other challenges to providing 3D conformal imaging systems exist when using scintillators to perform imaging.

BRIEF DESCRIPTION OF THE DRAWINGS

To facilitate further description of the embodiments, the following drawings are provided in which.

Figure 1:
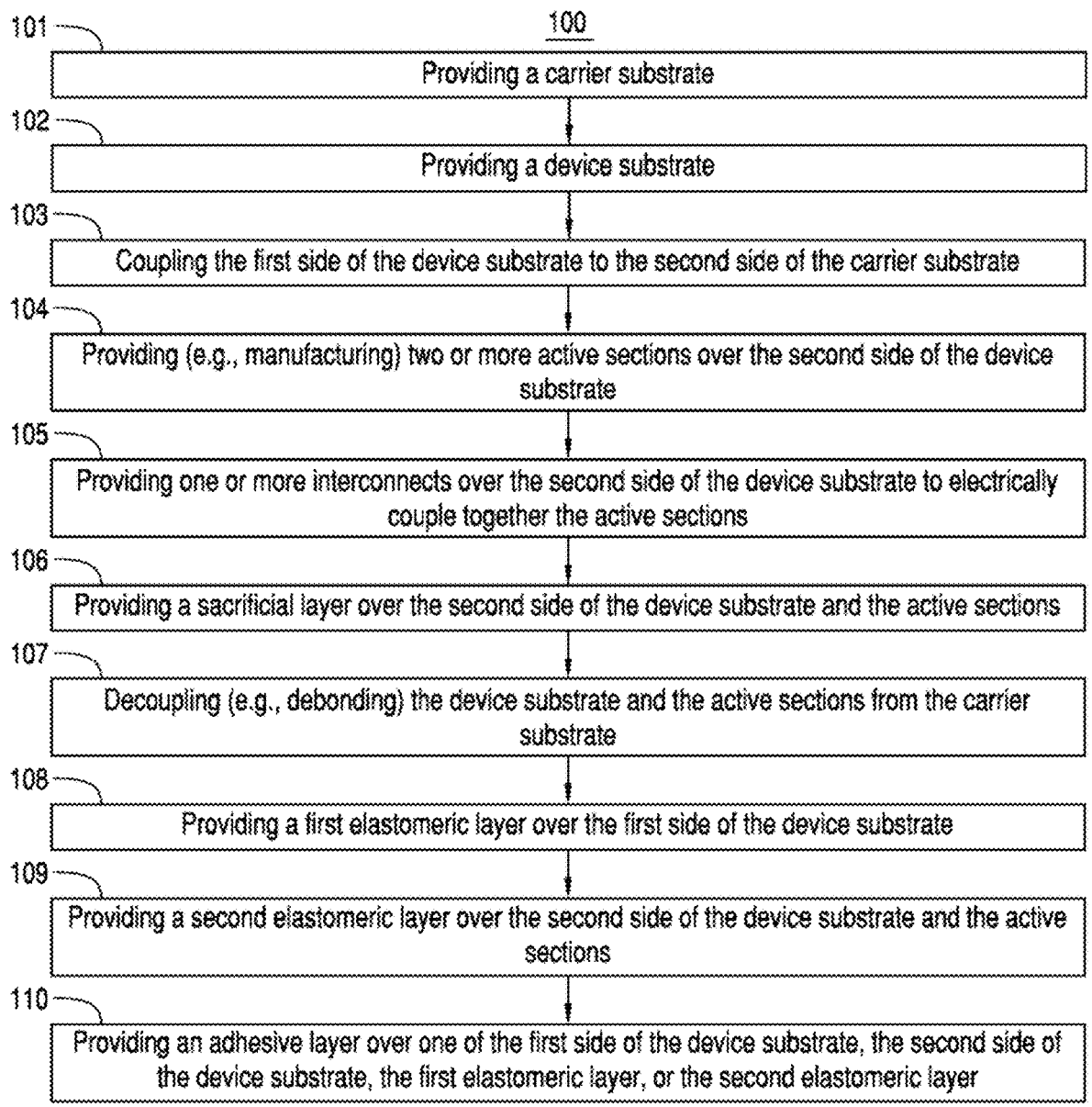
FIG. 1 illustrates an example of a method of providing an electronic device, according to an embodiment.

For simplicity and clarity of illustration, the drawing figures illustrate the general manner of construction, and descriptions and details of well-known features and techniques may be omitted to avoid unnecessarily obscuring the invention. Additionally, elements in the drawing figures are not necessarily drawn to scale. For example, the dimensions of some of the elements in the figures may be exaggerated relative to other elements to help improve understanding of embodiments of the present invention. The same reference numerals in different figures denote the same elements.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Furthermore, the terms "include," and "have," and any variations thereof, are intended to cover a non-exclusive inclusion, such that a process, method, system, article, device, or apparatus that comprises a list of elements is not necessarily limited to those elements, but may include other elements not expressly listed or inherent to such process, method, system, article, device, or apparatus.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments of the invention described herein are, for example, capable of operation in other orientations than those illustrated or otherwise described herein.

The terms "couple," "coupled," "couples," "coupling," and the like should be broadly understood and refer to connecting two or more elements or signals, electrically, mechanically and/or otherwise. Two or more electrical elements may be electrically coupled together but not be mechanically or otherwise coupled together; two or more mechanical elements may be mechanically coupled together, but not be electrically or otherwise coupled together; two or more electrical elements may be mechanically coupled together, but not be electrically or otherwise coupled together. Coupling may be for any length of time, e.g., permanent or semi-permanent or only for an instant.

An electrical "coupling" and the like should be broadly understood and include coupling involving any electrical signal, whether a power signal, a data signal, and/or other types or combinations of electrical signals. A mechanical "coupling" and the like should be broadly understood and include mechanical coupling of all types.

The absence of the word "removably," "removable," and the like near the word "coupled," and the like does not mean that the coupling, etc. in question is or is not removable.

The term "median plane" as used herein relative to a substrate, a semiconductor layer, or a portion of the substrate or semiconductor layer means a reference plane that is approximately equidistant from opposing first and second sides (e.g., bottom and top sides) or major surfaces of the particular substrate, semiconductor layer, or portion of the substrate or semiconductor layer. Meanwhile, the term "x-y plane" as used herein relative to a substrate, a semiconductor layer, or a portion of the substrate or semiconductor layer means a reference plane that is approximately parallel to opposing first and second sides (e.g., bottom and top sides) or major surfaces of the particular substrate, semiconductor layer, or portion of the substrate or semiconductor layer. In these or other embodiments, the "x-y plane" can comprise the "median plane," and vice versa. Further, the term "z-axis" as used herein relative to a substrate, a semiconductor layer, or a portion of the substrate or semiconductor layer means a reference axis extending approximately perpendicular to opposing first and second sides (e.g., bottom and top sides) or major surfaces of the particular substrate, semiconductor layer, or portion of the substrate or semiconductor layer.

The term "bowing" as used herein means the curvature of a substrate or a semiconductor layer about its median plane. The term "warping" as used herein means the linear displacement of a surface of a substrate or semiconductor layer with respect to its z-axis. The term "distortion" as used herein means the displacement of a substrate or semiconductor layer in its x-y plane. For example, distortion could include shrinkage or expansion of a substrate or semiconductor layer in its x-y plane.

The term "CTE matched material" and the like as used herein means a material that has a coefficient of thermal expansion (CTE) which differs from the CTE of a reference material by less than about 20 percent (%). Preferably, the CTEs differ by less than about 10%, 5%, 3%, or 1%.

The term "flexible substrate" as used herein means a free-standing substrate that readily adapts its shape. Accordingly, in many embodiments, the flexible substrate can comprise (e.g., consist of) a flexible material, and/or can comprise a thickness (e.g., an average thickness) that is sufficiently thin so that the substrate readily adapts in shape. In these or other embodiments, a flexible material can refer to a material having a low elastic modulus. Further, a low elastic modulus can refer to an elastic modulus of less than approximately five GigaPascals (GPa). In some embodiments, a substrate that is a flexible substrate because it is sufficiently thin so that it readily adapts in shape, may not be a flexible substrate if implemented with a greater thickness, and/or the substrate may have an elastic modulus exceeding five GPa. For example, the elastic modulus could be greater than or equal to approximately five GPa but less than or equal to approximately twenty GPa, fifty GPa, seventy GPa, or eighty GPa. Exemplary materials for a substrate that is a flexible substrate because it is sufficiently thin so that it readily adapts in shape, but that may not be a flexible substrate if implemented with a greater thickness, can comprise certain glasses (e.g., fluorosilicate glass, borosilicate glass, Corning® glass, Willow™ glass, and/or Vitrelle glass, etc., such as, for example, as manufactured by Corning Inc. of Corning, N.Y., United States of America, etc.) or silicon having a thickness greater than or equal to approximately 25 micrometers and less than or equal to approximately 100 micrometers.

The terms "elastomeric substrate" and/or "elastomeric layer" as used herein can mean a layer comprising one or more materials, having the properties of a flexible substrate, and also having a high yield strength. That is, the elastomeric substrate and/or elastomeric layer is a free-standing layer that readily adapts its shape and that substantially recovers (e.g., with little or no plastic deformation) from applied stresses and/or strains. Because applied stresses and/or strains depend on environment and implementation, in exemplary embodiments, a high yield strength can refer to a yield strength greater than or equal to approximately 2.00 MegaPascals, 4.14 MegaPascals, 5.52 MegaPascals, and/or 6.89 MegaPascals.

Meanwhile, the term "rigid substrate" as used herein can mean a free-standing substrate that does not readily adapt its shape and/or a substrate that is not a flexible substrate. In some embodiments, the rigid substrate can be devoid of flexible material and/or can comprise a material having an elastic modulus greater than the elastic modulus of a flexible substrate. In various embodiments, the rigid substrate can be implemented with a thickness that is sufficiently thick so that the substrate does not readily adapt its shape. In these or other examples, the increase in rigidity of the carrier substrate provided by increasing the thickness of the carrier substrate can be balanced against the increase in cost and weight provided by increasing the thickness of the carrier substrate.

As used herein, "polish" can mean to lap and polish a surface or to only lap the surface.

DETAILED DESCRIPTION

Some embodiments include an imaging system. The imaging system can comprise: a scintillator structure; and an electronic device engaged with the scintillator structure, wherein: the scintillator structure can comprise: a scintillator support layer; and a scintillator layer; the scintillator support layer can comprise: a first substantially non-planar surface; a second substantially non-planar surface, the first substantially non-planar surface can be approximately parallel to the second substantially non-planar surface; and a scintillator support layer thickness greater than approximately 200 micrometers and less than or equal to approximately 300 micrometers; the scintillator layer can comprise: a first surface; a second surface opposite the first surface, the second surface being configured to scintillate; and one or more granular phosphor materials that can comprise a diameter of greater than or equal to approximately 2 micrometers and less than or equal to approximately 30 micrometers; the first surface of the scintillator layer can be coupled to the second substantially non-planar surface of the scintillator support layer such that the second surface of the scintillator layer comprises a contour of the second substantially non-planar surface of the scintillator support layer; the electronic device can comprise a device substrate and one or more active sections; the device substrate can comprise a first surface and a second surface opposite the first surface of the device substrate; the one or more active sections are at the second surface of the device substrate; and the second surface of the device substrate and the one or more active sections can conform to the second surface of the scintillator layer.

Other embodiments include an imaging system. The imaging system can comprise: a scintillator structure; and an electronic device engaged with the scintillator structure, wherein: the scintillator structure can comprise: a scintillator support layer; and a scintillator layer; the scintillator support layer can comprise: a substantially non-planar surface; a test surface opposite and approximately parallel to the substantially non-planar surface; and a scintillator support layer thickness greater than approximately 200 micrometers and less than or equal to approximately 300 micrometers; the scintillator layer can comprise: a first surface; a second surface opposite the first surface, the second surface can be configured to scintillate; and one or more granular phosphor materials that can comprise a diameter of greater than or equal to approximately 2 micrometers and less than or equal to approximately 30 micrometers; the first surface of the scintillator layer can be coupled to the substantially non-planar surface of the scintillator support layer such that the second surface of the scintillator layer comprises a contour of the substantially non-planar surface of the scintillator support layer; the test surface of the scintillator support layer complements the contour of the substantially non-planar surface of the scintillator support layer; the electronic device can comprise a device substrate and one or more active sections; the device substrate can comprise a first surface and a second surface opposite the first surface of the device substrate; the one or more active sections are at the second surface of the device substrate; and the second surface of the device substrate and the one or more active sections conform to the second surface of the scintillator layer.

Some embodiments include a method of providing an electronic device. The method can comprise: providing a carrier substrate; providing a device substrate comprising a first side and a second side opposite the first side, the device substrate comprising a flexible substrate; coupling the first side of the device substrate to the carrier substrate; and after coupling the first side of the device substrate to the carrier substrate, providing two or more active sections over the second side of the device substrate, each active section of the two or more active sections being spatially separate from each other and comprising at least one semiconductor device.

Other embodiments include an electronic device. The electronic device comprises a device substrate comprising a first side and a second side opposite the first side. The device substrate can comprise a flexible substrate. Further, the electronic device comprises two or more active sections over the second side of the device substrate. Each active section of the two or more active sections can be spatially separate from each other and can comprise at least one semiconductor device. Further still, the electronic device can comprise one or more wavy metal interconnects over the second side of the device substrate electrically coupling together the two or more active sections.

Further embodiments include a method. The method can comprise: decoupling a sacrificial layer from an electronic device; and coupling the electronic device to organic tissue. The electronic device can comprise a device substrate comprising a first side and a second side opposite the first side. Meanwhile, the device substrate can comprise a flexible substrate. Further, the electronic device can comprise two or more active sections over the second side of the device substrate. Meanwhile, each active section of the two or more active sections can be spatially separate from each other and can comprise at least one semiconductor device. Further still, the electronic device can comprise one or more wavy metal interconnects over the second side of the device substrate electrically coupling together the two or more active sections, and the sacrificial layer over the second side of the device substrate and the two or more active sections.

Meanwhile, some embodiments include a method of providing an electronic device. The method can comprise providing a first device substrate. The first device substrate can comprise a first side and a second side opposite the first side, and can comprise a first flexible substrate, a first device portion, and a first perimeter portion at least partially framing the first device portion. Further, the method can comprise providing one or more first active sections over the second side of the first device substrate at the first device portion. Each first active section of the one or more first active sections can comprise at least one first semiconductor device, each first semiconductor device of the at least one first semiconductor device can comprise at least one first pixel, and each first pixel of the at least one first pixel can comprise a first smallest cross dimension. Further still, the method can comprise, after providing the one or more first active sections over the second side of the first device substrate at the first device portion, folding the first perimeter portion of the first device substrate toward the first device portion at the first side of the first device substrate so that a first edge portion remains to at least partially frame the first device portion. The first edge portion can comprise a first edge portion width dimension smaller than the first smallest cross dimension.

In these or other embodiments, the method can comprise providing a second device substrate. The second device substrate can comprise a first side and a second side opposite the first side, and can comprise a second flexible substrate, a second device portion, and a second perimeter portion at least partially framing the second device portion. Further, the method can comprise providing one or more second active sections over the second side of the second device substrate at the second device portion. Each second active section of the one or more second active sections can comprise at least one second semiconductor device, each second semiconductor device of the at least one second semiconductor device can comprise at least one second pixel, and each second pixel of the at least one second pixel can comprise a second smallest cross dimension. Further still, the method can comprise, after providing the one or more second active sections over the second side of the second device substrate at the second device portion, folding the second perimeter portion of the second device substrate toward the second device portion at the first side of the second device substrate so that a second edge portion remains to at least partially frame the second device portion. The second edge portion can comprise a second edge portion width dimension smaller than the second smallest cross dimension. Also, the method can comprise: after folding the first perimeter portion of the first device substrate toward the first device portion at the first side of the first device substrate and after folding the second perimeter portion of the second device substrate toward the second device portion at the first side of the second device substrate, arranging the first device substrate adjacent to the second device substrate in an array grid; after providing the one or more first active sections over the second side of the first device substrate at the first device portion, supporting the first device substrate; and after providing the one or more second active sections over the second side of the first device substrate at the first device portion, supporting the second device substrate. Meanwhile, the first edge portion width dimension can be less than or equal to approximately 20 micrometers, and the second edge portion width dimension can be less than or equal to approximately 20 micrometers.

Other embodiments include an electronic device. The electronic device comprises a first device substrate comprising a first side and a second side opposite the first side. The first device substrate can further comprise a first flexible substrate, a first device portion, and a first perimeter portion at least partially framing the first device portion. Further, the electronic device comprises one or more first active sections over the second side of the first device substrate at the first device portion. Each first active section of the first active section(s) comprises at least one first semiconductor device, each first semiconductor device of the first semiconductor device(s) comprises at least one first pixel, and each first pixel of the first pixel(s) comprises a first smallest cross dimension. The first perimeter portion can comprise a first edge portion that at least partially frames the first device portion. Meanwhile, at least part of the first perimeter portion can form a first angle with the first device portion, the first angle can be less than or equal to approximately 90 degrees, and the first edge portion can comprise a first edge portion width dimension smaller than the first smallest cross dimension.

Some embodiments include a method. The method can comprise providing a scintillator structure. Meanwhile, providing the scintillator structure can comprise: providing a scintillator support layer; providing a scintillator layer; and coupling the scintillator layer to the scintillator support layer. Further, the scintillator support layer can comprise a substantially non-planar surface, the scintillator layer can comprise a first surface and a second surface opposite the first surface and being configured to scintillate, and the first surface of the scintillator layer can be coupled to the substantially non-planar surface of the scintillator support layer such that the second surface of the scintillator layer comprises a contour of the substantially non-planar surface of the scintillator support layer.

Further embodiments include a method. The method can comprise: providing a scintillator structure; providing an electronic device; and after providing the scintillator structure, engaging the electronic device with the scintillator structure. Meanwhile, providing the scintillator structure can comprise: providing a scintillator support layer; providing a scintillator layer; and coupling the scintillator layer to the scintillator support layer. Further, the scintillator support layer can comprise a substantially non-planar surface and a test surface opposite the substantially non-planar surface, the scintillator layer can comprise a first surface and a second surface opposite the first surface and being configured to scintillate, the first surface of the scintillator layer can be coupled to the substantially non-planar surface of the scintillator support layer such that the second surface of the scintillator layer comprises a contour of the substantially non-planar surface of the scintillator support layer, and the test surface of the scintillator support layer can complement the contour of the substantially non-planar surface of the scintillator support layer. Also, providing the electronic device can comprise: providing a device substrate comprising a first surface and a second surface opposite the first surface; and providing one or more active sections, the one or more active sections being over the second surface of the device substrate. Further still, when the electronic device is engaged with the scintillator structure, the second surface of the device substrate and the one or more active sections can conform to the second surface of the scintillator layer of the scintillator structure, the device substrate can further comprise a flexible substrate, each active section of the one or more active sections can comprise at least one semiconductor device, and each semiconductor device of the at least one semiconductor device can comprise at least one detector pixel.

Other embodiments include an imaging system. The imaging system comprises a scintillator structure. Meanwhile, the scintillator structure can comprise a scintillator support layer and a scintillator layer. Further, the scintillator support layer can comprise a substantially non-planar surface, the scintillator layer can comprise a first surface and a second surface opposite the first surface and is configured to scintillate, and the first surface of the scintillator layer can be coupled to the substantially non-planar surface of the scintillator support layer such that the second surface of the scintillator layer comprises a contour of the substantially non-planar surface of the scintillator support layer.

Turning to the drawings, FIG. 1 illustrates an example of a method 100 of providing an electronic device, according to an embodiment. Method 100 is merely exemplary and is not limited to the embodiments presented herein. Method 100 can be employed in many different embodiments or examples not specifically depicted or described herein. In some embodiments, the activities of method 100 can be performed in the order presented. In other embodiments, the activities of method 100 can be performed in any other suitable order. In still other embodiments, one or more of the activities in method 100 can be combined or skipped. Although the electronic device can comprise any suitable electronic device, in many embodiments, the electronic device can comprise a wearable consumer electronic device (e.g., a transdermal smart bandage). Further, the electronic device (e.g., wearable consumer electronic device) can comprise one or more flat panel electronic displays, one or more bioelectronic devices (e.g., biological sensors), etc. In these or other embodiments, the electronic device can comprise a deformable electronic device. Accordingly, the electronic device can be flexible and/or stretchable. As discussed in greater detail herein, the flexibility and/or stretchability of the electronic device can depend on the material properties of the device substrate and/or the elastomeric layer implemented with the electronic device.

Figure 2:
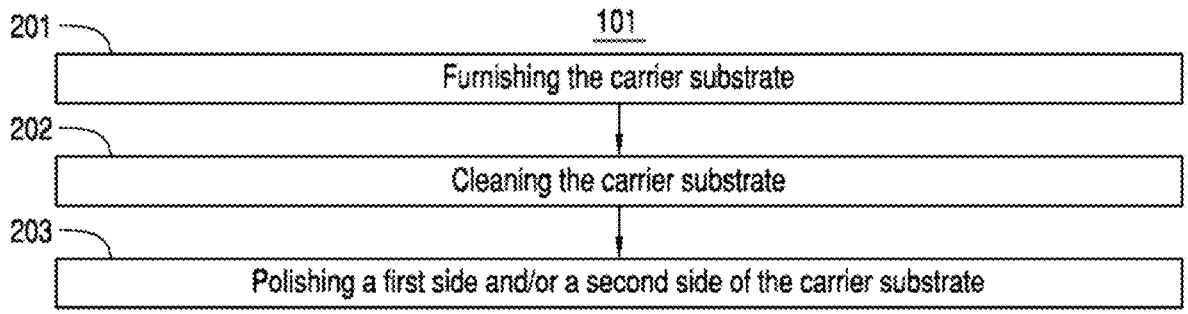
FIG. 2 illustrates an exemplary activity of providing a carrier substrate of the electronic device, according to the embodiment of FIG. 1.

Method 100 can comprise activity 101 of providing a carrier substrate. FIG. 2 illustrates an exemplary activity 101, according to the embodiment of FIG. 1.

For example, activity 101 can comprise activity 201 of furnishing the carrier substrate. The carrier substrate can comprise a first side and a second side opposite the first side. The carrier substrate can be configured to minimize bowing, warping, and/or distortion of the device substrate when the device substrate is coupled to the carrier substrate, as described below.

In many embodiments, the carrier substrate can comprise a rigid substrate. The carrier substrate (e.g., rigid substrate) can comprise any suitable material(s) having the characteristics of a rigid substrate as defined above. Specifically, exemplary material(s) can comprise alumina ($Al_2O_3$), silicon, glass (e.g., barium borosilicate, soda lime silicate, and/or an alkali silicate), metal (e.g., steel, such as, for example, stainless steel), and/or sapphire. However, in some embodiments, the carrier substrate (e.g., rigid substrate) can be devoid of silicon and/or amorphous silicon. Meanwhile, in many embodiments, the glass can comprise a low CTE glass.

Further, material(s) for the carrier substrate (e.g., rigid substrate) also can be selected so that a CTE of the material(s) approximately matches a CTE of the material(s) of the device substrate, which is introduced briefly above and described in greater detail below. Likewise, in some embodiments, material(s) for the device substrate can be selected so as to be CTE matched with the material(s) of the carrier substrate. Non-matched CTEs can create stress between the carrier substrate and the device substrate, which can result in bowing, warping, and/or distortion of the device substrate when the device substrate is coupled to the carrier substrate.

Meanwhile, in many embodiments, the carrier substrate can be a wafer or panel. The wafer or panel can comprise any suitable dimensions (e.g., diameter, thickness, length, width, etc.), as applicable. In some embodiments, the wafer or panel can comprise a largest dimension (e.g., diameter, length) of approximately 6 inches (approximately 15.24 centimeters), approximately 8 inches (approximately 20.32 centimeters), approximately 12 inches (approximately 30.48 centimeters), or approximately 18 inches (approximately 45.72 centimeters), such as, for example, in the x-y plane and/or median plane of the carrier substrate. In some embodiments, the carrier substrate can be a panel of approximately 370 mm in width by approximately 470 mm in length in the x-y plane and/or median plane of the carrier substrate. In some examples, the wafer or panel can comprise a thickness of at least approximately 0.5 millimeters. The thickness dimension of the carrier substrate can refer to a distance between the first and second sides of the carrier substrate measured approximately parallel to the z-axis of the carrier substrate. In many embodiments, the thickness dimension of the carrier substrate can be approximately constant.

Later, in some embodiments, activity 101 can comprise activity 202 of cleaning the carrier substrate. In some embodiments, activity 202 can be performed by cleaning the carrier substrate with plasma (e.g., oxygen plasma) or with an ultrasonic bath.

Then, activity 101 can comprise activity 203 of polishing a first side and/or a second side of the carrier substrate. Polishing the side of the carrier substrate (e.g., the first side) that is not subsequently coupled (e.g., bonded) with the device substrate, as described below, improves the ability of a vacuum or air chuck to handle the carrier substrate. Also, polishing the surface of the carrier substrate (e.g., the second side) that is subsequently coupled (e.g., bonded) to the device substrate, as described below, removes topological features at that side of the carrier substrate that could cause roughness of the resulting device substrate assembly in the z-axis after the device substrate and carrier substrate are coupled together.

Referring now back to FIG. 1, method 100 comprises activity 102 of providing a device substrate. Like the carrier substrate, the device substrate can comprise a first side and a second side opposite the first side. Activity 102 can be performed before, after, or approximately simultaneously with activity 101.

In many embodiments, the device substrate can comprise a flexible substrate. The device substrate (e.g., flexible substrate) can comprise any suitable material(s) having the characteristics of a flexible substrate as defined above. Specifically, exemplary material(s) can comprise polyethylene naphthalate, polyethylene terephthalate, polyethersulfone, polyimide, polyamide, polycarbonate, cyclic olefin copolymer, liquid crystal polymer, any other suitable polymer, glass (e.g., fluorosilicate glass, borosilicate glass, Corning® glass, Willow™ glass, and/or Vitrelle glass, etc., such as, for example, as manufactured by Corning Inc. of Corning, N.Y., United States of America, etc.), metal foil (e.g., aluminum foil, etc.), etc. In these or other embodiments, the device substrate can comprise an elastic modulus of less than approximately five GigaPascals.

Further, the device substrate can comprise a thickness dimension. The thickness dimension of the device substrate can refer to a distance between the first and second sides of the device substrate measured approximately parallel to the z-axis of the device substrate. For example, the thickness dimension of the device substrate can be greater than or equal to approximately 1 micrometer and less than or equal to approximately 1 millimeter. In these or other embodiments, the thickness dimension of the device substrate can be less than or equal to approximately 10, 20, or 25 micrometers. In many embodiments, the thickness dimension of the device substrate can be approximately constant.

In many embodiments, activity 102 can comprise an activity of furnishing the device substrate. In some embodiments, activity 102 can comprise an activity of depositing the device substrate over the second side of the carrier substrate. In many embodiments, the depositing the device substrate over the second side of the carrier substrate can be performed using any suitable deposition technique(s) (e.g., chemical vapor deposition, such as, for example plasma-enhanced chemical vapor deposition, sputtering, molecular beam epitaxy, spin-coating, spray-coating, extrusion coating, preform lamination, slot die coating, screen lamination, and/or screen printing, etc.). For example, in some embodiments, the depositing the device substrate over the second side of the carrier substrate can be performed as described in International Patent Application No. PCT/US2015/029991, filed on May 8, 2015 and which published as International Patent Application Publication No. WO 2015/175353 on Nov. 19, 2015. Accordingly, International Patent Application No. PCT/US2015/029991 is incorporated by reference in its entirety. In these embodiments, activity 103 (below) can be performed as part of activity 102.

Figure 3:
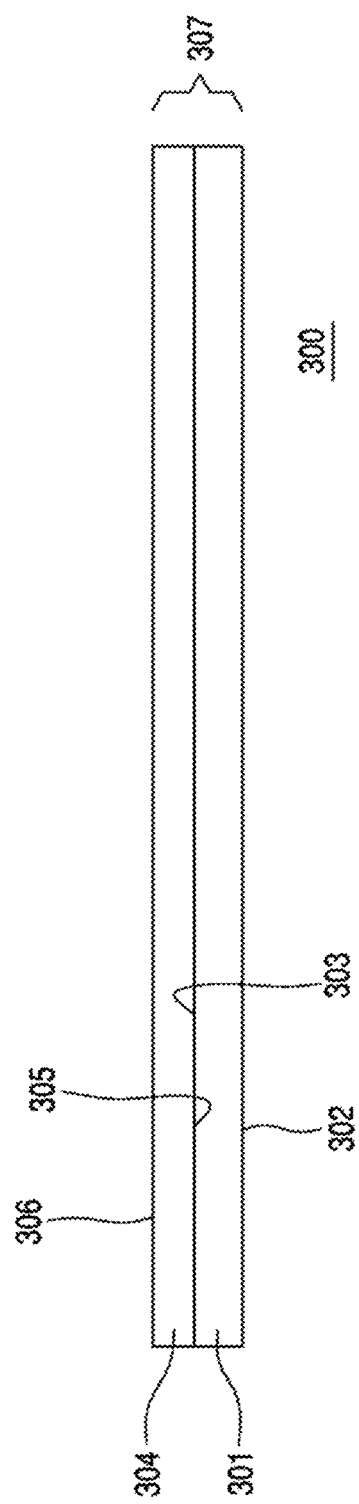
FIG. 3 illustrates a partial cross-sectional view of an electronic device after coupling a first side of a device substrate having the first side and a second side to the second side of a carrier substrate having a first side and the second side to provide a substrate assembly, according to the embodiment of FIG. 1.

Referring again to FIG. 1, method 100 can comprise activity 103 of coupling the first side of the device substrate to the second side of the carrier substrate. Turning forward briefly in the drawings, FIG. 3 illustrates a partial cross-sectional view of an electronic device 300 after coupling a first side 305 of a device substrate 304 having the first side 305 and a second side 306 to the second side 303 of a carrier substrate 301 having a first side 302 and the second side 303 to provide substrate assembly 307, according to the embodiment of FIG. 1. In these or other embodiments, electronic device 300 can be similar or identical to the electronic device of method 100 (FIG. 1). Accordingly, device substrate 304 can be similar or identical to the device substrate of method 100 (FIG. 1), and carrier substrate 301 can be similar or identical to the carrier substrate of method 100 (FIG. 1).

Turning again to FIG. 1, in many embodiments, activity 103 is performed after activity 101. In these or other embodiments, activity 103 can be performed simultaneously with and/or after activity 102. In some embodiments, activity 103 can be performed as part of activity 102, as described above.

In various embodiments, performing activity 103 can comprise an activity of bonding the first side of the flexible substrate to the second side of the carrier substrate with an adhesive. The adhesive can be any suitable type of adhesive (e.g., a cross-linking adhesive). In many embodiments, the bonding the first side of the flexible substrate to the second side of the carrier substrate with the adhesive can be performed using any suitable bonding technique. For example, in some embodiments, the bonding the first side of the flexible substrate to the second side of the carrier substrate with the adhesive can be performed as described in any of (i) U.S. Non-Provisional patent application Ser. No. 13/118,225, filed May 27, 2011 and which issued as U.S. Pat. No. 8,481,859 on Jul. 9, 2013, (ii) U.S. Non-Provisional patent application Ser. No. 13/298,451, filed Nov. 17, 2011 and which issued as U.S. Pat. No. 8,999,778 on Apr. 7, 2015, (iii) U.S. Non-Provisional patent application Ser. No. 13/683,950, filed Nov. 21, 2012 and which issued as U.S. Pat. No. 8,992,712 on Mar. 31, 2015, (iv) U.S. Non-Provisional patent application Ser. No. 14/288,771, filed May 28, 2014 and which published as United States Patent Application Publication No. 2014/0254113 on Sep. 11, 2014, (v) U.S. Non-Provisional patent application Ser. No. 15/096,772, filed Apr. 12, 2016 and which published as United States Patent Application Publication No. 2016/0225653 on Aug. 4, 2016, (vi) U.S. Non-Provisional patent application Ser. No. 15/217,405, filed on Jul. 22, 2016, and/or (vii) International Patent Application No. PCT/US2015/029991, filed on May 8, 2015 and which published as International Patent Application Publication No. WO 2015/175353 on Nov. 19, 2015. Accordingly, U.S. Non-Provisional patent application Ser. No. 13/118,225, U.S. Non-Provisional patent application Ser. No. 13/298,451, U.S. Non-Provisional patent application Ser. No. 13/683,950, U.S. Non-Provisional patent application Ser. No. 14/288,771, International Patent Application No. PCT/US2014/060501, U.S. Non-Provisional patent application Ser. No. 15/217,405, and International Patent Application No. PCT/US2015/029991 each are incorporated by reference in their entirety.

In other embodiments, performing activity 103 can comprise an activity of depositing the device substrate over the second side of the carrier substrate. In these embodiments, the activity of depositing the device substrate over the second side of the carrier substrate can be performed as described above with respect to activity 102.

In various embodiments, after activity 103 is performed, the device substrate can be cured (e.g., thermally cured), such as, for example, at a temperature of approximately 350° C.

Referring back to FIG. 1, method 100 comprises activity 104 of providing (e.g., manufacturing) two or more active sections over the second side of the device substrate. Notably, in many embodiments, each of the active sections can be provided (e.g., manufactured) approximately simultaneously with each other. Further, activity 104 can be performed after activity 103.

In these or other embodiments, the active sections can be arranged apart (e.g., spatially separate, isolated, etc.) from each other and/or each can comprise at least one semiconductor device. In essence, the active sections can comprise semiconductor device islands arranged over the second side of the device substrate. By arranging the active sections apart from each other over the device substrate, the electronic device can be deformable (e.g., flexible and/or stretchable), as discussed in greater detail below. As a result, the electronic device can be implemented as a wearable consumer electronic device able to conform with uneven and/or pliable surfaces (e.g., organic tissue, etc.).

In some embodiments, the active sections can be uniformly arranged over the device substrate, though other arrangements (e.g., random arrangements) can also be implemented. In some embodiments, two or more of the active sections can be similar or identical to each other. In these or other embodiments, two or more of the active sections can be different from each other.

As described in greater detail below, in many embodiments, activity 104 can be performed by providing excess active section material over the second side of the device substrate and removing (e.g., etching) part of the active section material so that the active sections remain, but in other embodiments, the active sections can be provided (e.g., manufactured) by selective deposition over the second side of the device substrate. However, in some examples, selective deposition may require performing additional manufacturing activities that may lead to increased manufacturing costs.

Advantageously, as explained in greater detail below, the active sections can be provided (e.g., manufactured) over the device substrate (e.g., flexible substrate) with direct integration rather than with a multi-stage process of providing the active sections over one or more other substrates and then transferring the active sections to the device substrate (e.g., flexible substrate). Moreover, as noted, the active sections can be provided (e.g., manufactured) approximately simultaneously so the need to systematically and/or individually couple (e.g., bond) each of the active sections to the device substrate (e.g., flexible substrate) can be avoided. These advantages can improve manufacturability and decrease manufacturing costs.

Further, many embodiments of method 100 can leverage the inherent scalability advantages of conventional flat panel electronic display manufacturing technologies, which currently use flexible substrates approaching lateral dimensions of approximately 10 square meters. Accordingly, un-functionalized manufacturing costs can be reduced, and because the flat panel electronic display industrial base is already well established and capable of annually supplying the electronic devices required to transition wearable consumer electronic devices from the laboratory to market. For perspective, flat panel electronic displays in 2012 were manufactured at a rate of 100 square kilometers per year. Accordingly, if just one percent (1%) of the existing flat panel electronic display industrial capacity was diverted to manufacture large area wearable consumer electronic devices, approximately seven hundred thousand people each year could be covered entirely from head to toe with wearable consumer electronic devices. Further, assuming an average area of twenty five square centimeters for each smart bandage, approximately four hundred million smart bandages could be manufactured annually.

Figure 4:
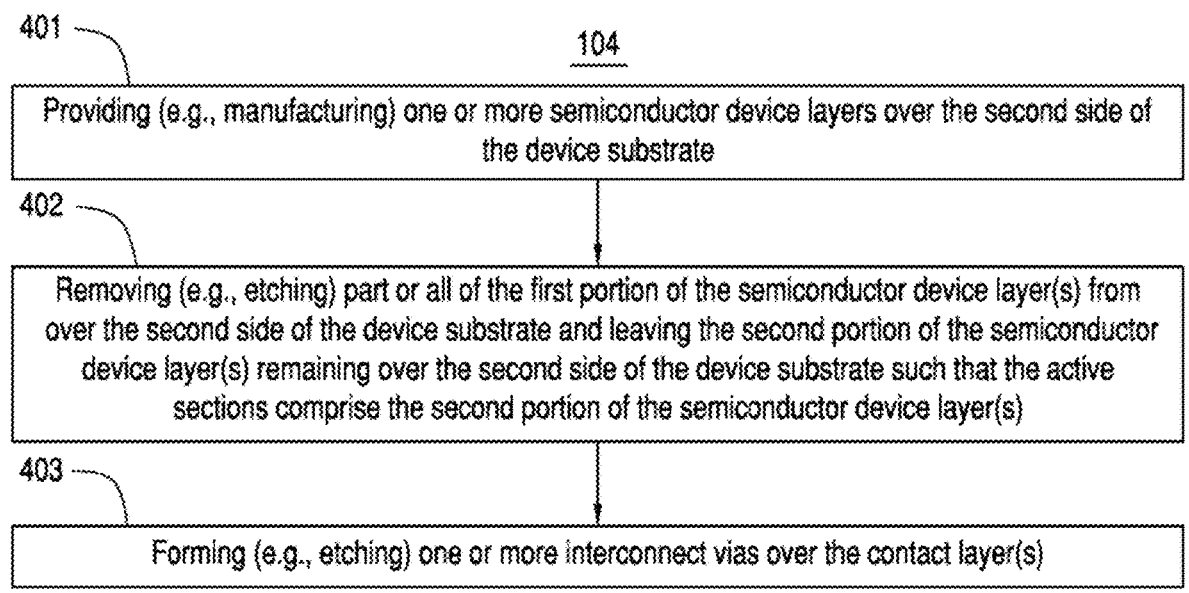
FIG. 4 illustrates an exemplary activity of providing (e.g., manufacturing) two or more active sections of the electronic device over a second side of a device substrate of the electronic device, according to the embodiment of FIG. 1.

Recognizing that method 100 can leverage conventional flat panel electronic display manufacturing techniques, FIG. 4 illustrates an exemplary activity 104, according to the embodiment of FIG. 1. To begin with, activity 104 can comprise activity 401 of providing (e.g., manufacturing) one or more semiconductor device layers over the second side of the device substrate. In general, activity 401 can be performed after activities 101-103. In many embodiments, the semiconductor device layer(s) can be provided (e.g., manufactured) over the second side of the device substrate by deposition. When the semiconductor device layer(s) are provided over the second side of the device substrate by deposition, the deposition can be performed using any suitable deposition technique(s) (e.g., chemical vapor deposition, such as, for example plasma-enhanced chemical vapor deposition, sputtering, molecular beam epitaxy, spin-coating, spray-coating, extrusion coating, preform lamination, slot die coating, screen lamination, and/or screen printing, etc.) and/or under any deposition condition(s) suitable for the material(s) elected for the first semiconductor device layer(s), the device substrate, and/or the carrier substrate.

For example, in these or other embodiments, the providing (e.g., manufacturing) one or more semiconductor device layers over the second side of the device substrate can be performed as described in any of (i) U.S. Non-Provisional patent application Ser. No. 13/298,451, filed Nov. 17, 2011 and which issued as U.S. Pat. No. 8,999,778 on Apr. 7, 2015, (ii) U.S. Non-Provisional patent application Ser. No. 13/683,950, filed Nov. 21, 2012 and which issued as U.S. Pat. No. 8,992,712 on Mar. 31, 2015, (iii) U.S. Non-Provisional patent application Ser. No. 13/684,150, filed Nov. 21, 2012 and which issued as U.S. Pat. No. 9,076,822 on Jul. 7, 2015, (iv) U.S. Non-Provisional patent application Ser. No. 14/029,502, filed Sep. 17, 2013 and which published as United States Patent Application Publication No. 2014/0008651 on Jan. 9, 2014, (v) U.S. Non-Provisional patent application Ser. No. 14/288,771, filed May 28, 2014 and which published as United States Patent Application Publication No. 2014/0254113 on Sep. 11, 2014, (vi) U.S. Non- Provisional patent application Ser. No. 14/642,550, filed Mar. 9, 2015 and which published as United States Patent Application Publication No. 2016/0260765 on Sep. 8, 2016, (vii) U.S. Non-Provisional patent application Ser. No. 14/642,563, filed Mar. 9, 2015 and which published as United States Patent Application Publication No. 2016/0260768 on Sep. 8, 2016, (viii) U.S. Non-Provisional patent application Ser. No. 15/096,772, filed Apr. 12, 2016 and which published as United States Patent Application Publication No. 2016/0225653 on Aug. 4, 2016, (ix) U.S. Non-Provisional patent application Ser. No. 15/217,405, filed on Jul. 22, 2016, and/or (x) International Patent Application No. PCT/US2015/029991, filed on May 8, 2015 and which published as International Patent Application Publication No. WO 2015/175353 on Nov. 19, 2015. Accordingly, U.S. Non-Provisional patent application Ser. No. 13/298,451, U.S. Non-Provisional patent application Ser. No. 13/683,950, U.S. Non-Provisional patent application Ser. No. 13/684,150, U.S. Non-Provisional patent application Ser. No. 14/029,502, U.S. Non-Provisional patent application Ser. No. 14/288,771, U.S. Non-Provisional patent application Ser. No. 14/642,550, U.S. Non-Provisional patent application Ser. No. 14/642,563, U.S. Non-Provisional patent application Ser. No. 15/096,772, U.S. Non-Provisional patent application Ser. No. 15/217,405, and/or (ix) International Patent Application No. PCT/US2015/029991 each are incorporated by reference in their entirety. In further embodiments, the semiconductor device layer(s) can be provided (e.g., manufactured) over the second side of the device substrate with an electronics on plastic by laser release (EPLaR™) manufacturing technique. EPLaR™ manufacturing allows flexible thin film electronics (e.g., flat panel displays) to be fabricated using existing high temperature (e.g., greater than or equal to approximately 300° C.) commercial thin film electronics manufacturing process tooling and process steps.

Figure 5:
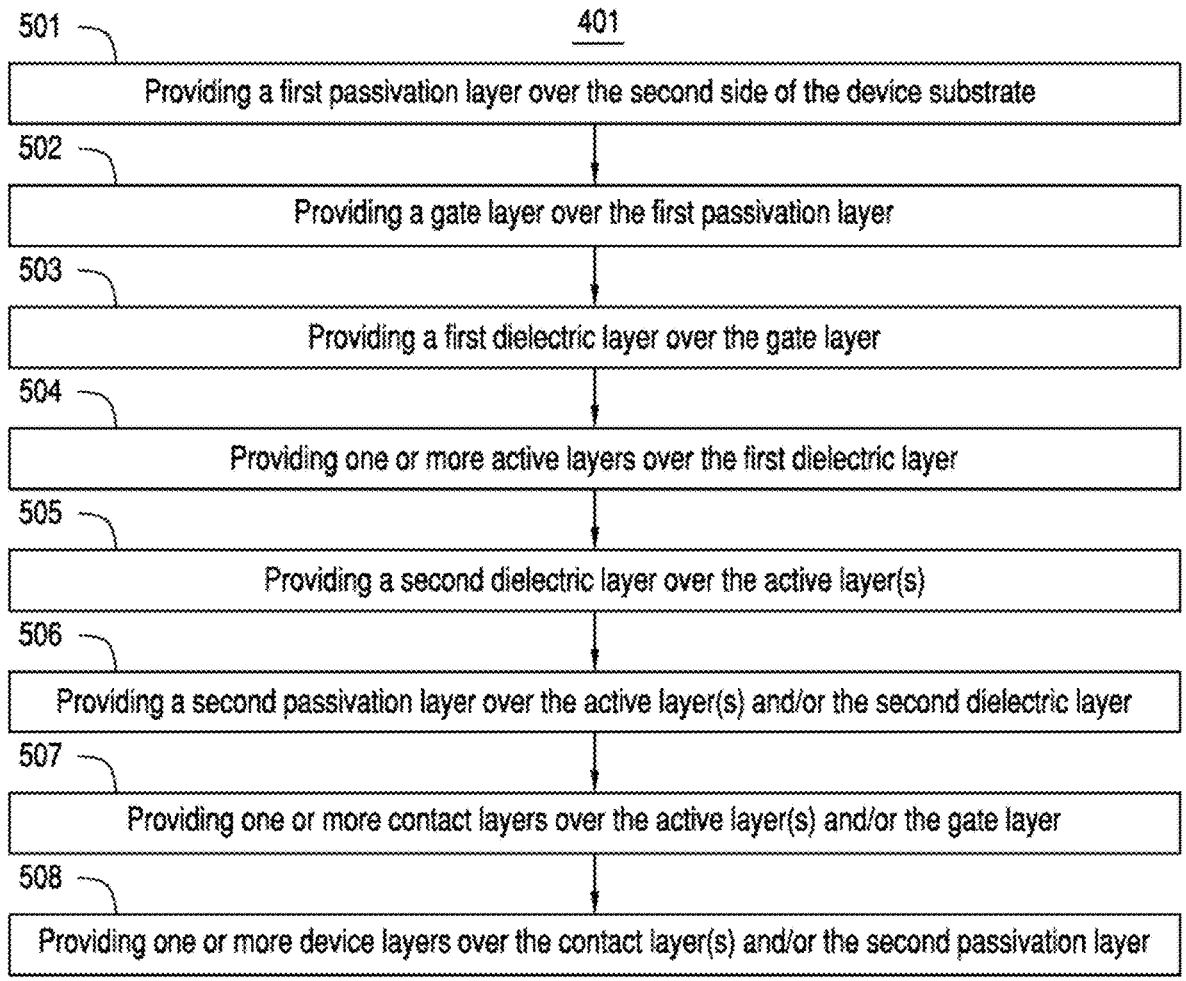
FIG. 5 illustrates an exemplary activity of providing (e.g., manufacturing) one or more semiconductor device layers of the electronic device over the second side of the device substrate, according to the embodiment of FIG. 1.

Turning to the next drawing, FIG. 5 illustrates an exemplary activity 401, according to the embodiment of FIG. 1. For example, activity 401 can comprise activity 501 of providing a first passivation layer over the second side of the device substrate. In many embodiments, the first passivation layer can comprise silicon nitride. However, any material(s) suitable to protect the device substrate during subsequent semiconductor manufacturing activities can be implemented. For example, the first passivation layer can be operable as a moisture barrier and/or a chemical barrier to protect the device substrate from the caustic chemicals used during activity 401.

Further, activity 401 can comprise activity 502 of providing a gate layer over the first passivation layer. The gate layer can comprise a conductive material. For example, in many embodiments, the conductive material can comprise molybdenum and/or aluminum.

Further, activity 401 can comprise activity 503 of providing a first dielectric layer over the gate layer. In many embodiments, the first dielectric layer can comprise silicon nitride. Other dielectric materials can also be implemented.

Further, activity 401 can comprise activity 504 of providing one or more active layers over the first dielectric layer. In many embodiments, the active layer(s) can comprise amorphous silicon and/or one or more metal oxides (e.g., indium oxide, zinc oxide, gallium oxide, tin oxide, hafnium oxide, aluminum oxide, etc.).

Further, activity 401 can comprise activity 505 of providing a second dielectric layer over the active layer(s). In many embodiments, the second dielectric layer can comprise silicon nitride. Other dielectric materials can also be implemented.

Further, activity 401 can comprise activity 506 of providing a second passivation layer over the active layer(s) and/or the second dielectric layer. In many embodiments, the second passivation layer can comprise silicon nitride.

Figure 6:
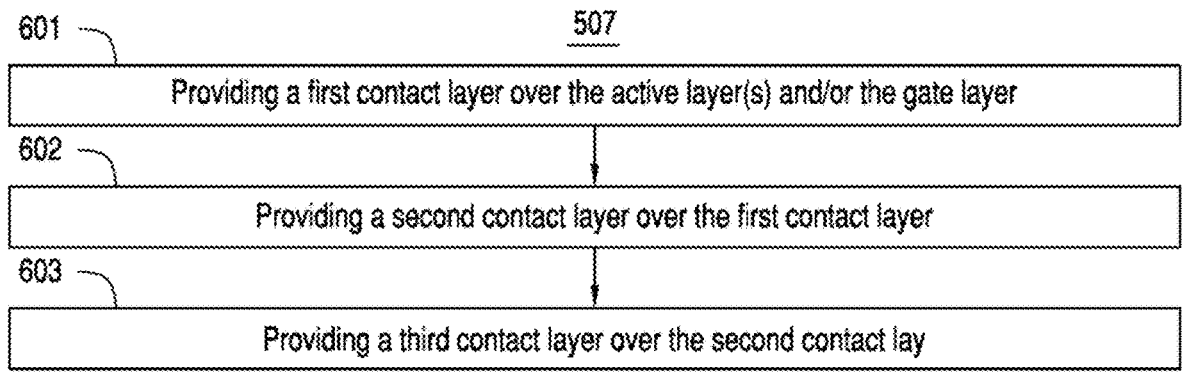
FIG. 6 illustrates an exemplary activity of providing one or more contact layers of the semiconductor layer(s) over one or more active layer and/or a gate layer of the semiconductor layers, according to the embodiment of FIG. 1.

Further, activity 401 can comprise activity 507 of providing one or more contact layers over the active layer(s) and/or the gate layer. FIG. 6 illustrates an exemplary activity 507, according to the embodiment of FIG. 1.

For example, activity 507 can comprise activity 601 of providing a first contact layer over the active layer(s) and/or the gate layer. In many embodiments, the first contact layer can comprise N+ amorphous silicon.

Further, activity 507 can comprise activity 602 of providing a second contact layer over the first contact layer. In many embodiments, the second contact layer can be configured to prevent movement by diffusion of atoms from a third contact layer (below) into the first contact layer. According, in some embodiments, the second contact layer can comprise tantalum.

Further, activity 507 can comprise activity 603 of providing a third contact layer over the second contact layer. The third contact layer can comprise a conductive material. Exemplary conductive materials can comprise molybdenum and/or aluminum.

Turning now back to FIG. 5, activity 401 can comprise activity 508 of providing one or more device layers over the contact layer(s) and/or the second passivation layer. In these or other embodiments, the various layer(s) provided in activities 501-507 can provide one or more thin film transistors, and the device layer(s) can provide one or more electronic components (e.g., electronic emitters, sensors, etc.) coupled to the thin film transistor(s). Together, the thin film transistor(s) and the electronic component(s) can comprise the semiconductor device(s) of the active sections of method 100 (FIG. 1) and/or activity 104 (FIG. 1).

Notably, in many embodiments, one or more of activity 401 (FIG. 4), activities 501-508 and/or activities 601-603 (FIG. 6) can comprise one or more patterning activities in which the various layers of activities 501-508 and/or activities 601-603 can be patterned, as desirable. These patterning activities can be performed using conventional semiconductor patterning techniques and/or the patterning activities described in one or more of (i) U.S. Non-Provisional patent application Ser. No. 13/298,451, filed Nov. 17, 2011 and which issued as U.S. Pat. No. 8,999,778 on Apr. 7, 2015, (ii) U.S. Non-Provisional patent application Ser. No. 13/683, 950, filed Nov. 21, 2012 and which issued as U.S. Pat. No. 8,992,712 on Mar. 31, 2015, (iii) U.S. Non-Provisional patent application Ser. No. 13/684,150, filed Nov. 21, 2012 and which issued as U.S. Pat. No. 9,076,822 on Jul. 7, 2015, (iv) U.S. Non-Provisional patent application Ser. No. 14/029,502, filed Sep. 17, 2013 and which published as United States Patent Application Publication No. 2014/0008651 on Jan. 9, 2014, (v) U.S. Non-Provisional patent application Ser. No. 14/288,771, filed May 28, 2014 and which published as United States Patent Application Publication No. 2014/0254113 on Sep. 11, 2014, (vi) U.S. Non-Provisional patent application Ser. No. 14/642,550, filed Mar. 9, 2015 and which published as United States Patent Application Publication No. 2016/0260765 on Sep. 8, 2016, (vii) U.S. Non-Provisional patent application Ser. No. 14/642,563, filed Mar. 9, 2015 and which published as United States Patent Application Publication No. 2016/0260768 on Sep. 8, 2016, (viii) U.S. Non-Provisional patent application Ser. No. 15/096,772, filed Apr. 12, 2016 and which published as United States Patent Application Publication No. 2016/0225653 on Aug. 4, 2016, (ix) U.S. Non-Provisional patent application Ser. No. 15/217,405, filed on Jul. 22, 2016, and/or (x) International Patent Application No. PCT/US2015/029991, filed on May 8, 2015 and which published as International Patent Application Publication No. WO 2015/175353 on Nov. 19, 2015. Accordingly, U.S. Non-Provisional patent application Ser. No. 13/298,451, U.S. Non-Provisional patent application Ser. No. 13/683,950, U.S. Non-Provisional patent application Ser. No. 13/684,150, U.S. Non-Provisional patent application Ser. No. 14/029,502, U.S. Non-Provisional patent application Ser. No. 14/288,771, U.S. Non-Provisional patent application Ser. No. 14/642,550, U.S. Non-Provisional patent application Ser. No. 14/642,563, U.S. Non-Provisional patent application Ser. No. 15/096,772, U.S. Non-Provisional patent application Ser. No. 15/217,405, and International Patent Application No. PCT/US2015/029991 each are incorporated by reference in their entirety.

Figure 7:
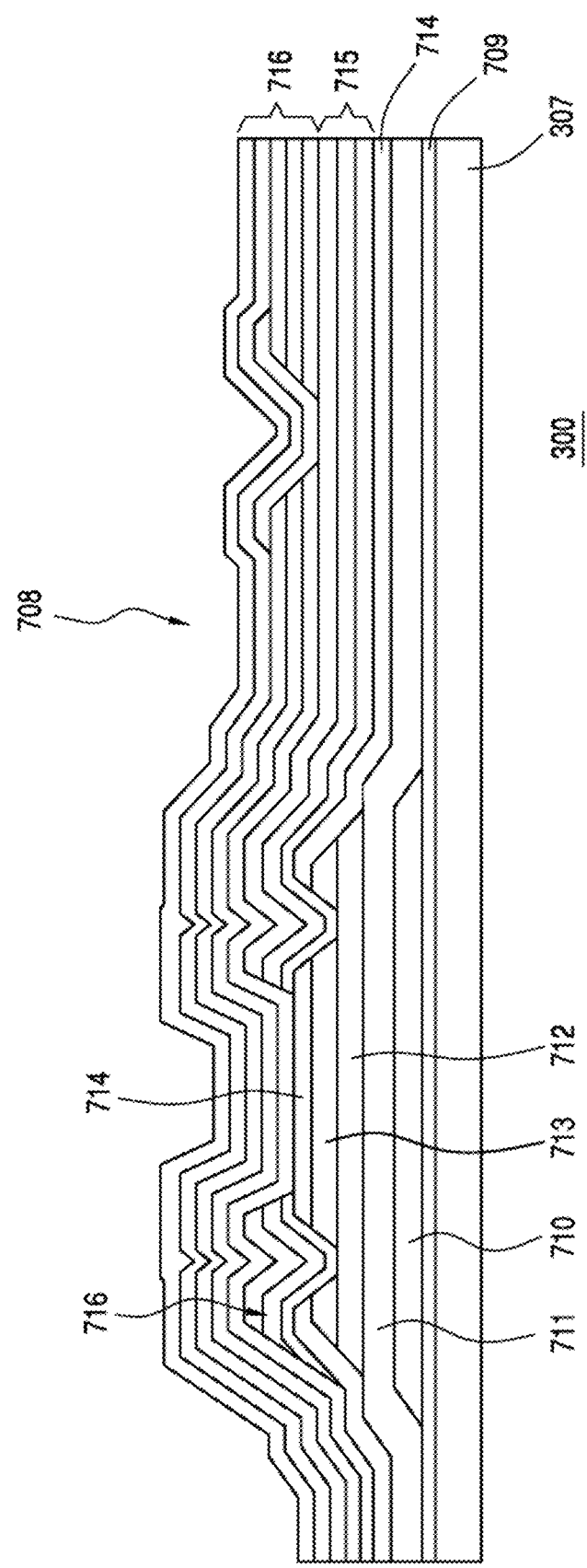
FIG. 7 illustrates a partial cross-sectional view of the electronic device of FIG. 3 in a device build area of the electronic device after providing one or more semiconductor device layers over the substrate assembly.
Figure 8:
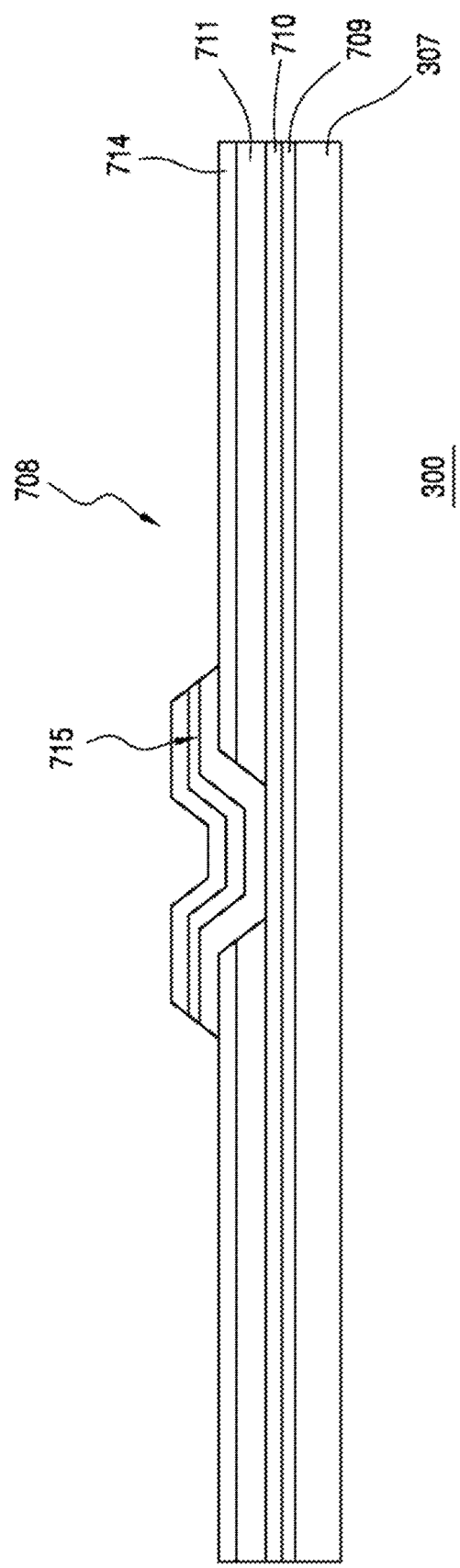
FIG. 8 illustrates a partial cross-sectional view of the electronic device of FIG. 3 in a gate contact build area of the electronic device after providing the semiconductor device layer(s) over the substrate assembly.

Turning ahead in the drawings, FIG. 7 illustrates a partial cross-sectional view of electronic device 300 in a device build area of electronic device 300 after providing one or more semiconductor device layers 708 over substrate assembly 307, according to the embodiment of FIG. 3. For example, first passivation layer 709 is provided over substrate assembly 307, gate layer 710 is provided over first passivation layer 709, first dielectric layer 711 is provided over gate layer 710, one or more active layers 712 are provided over first dielectric layer 711, second dielectric layer 713 is provided over active layer(s) 712, second passivation layer 714 is provided over second dielectric layer 713, contact layer(s) 715 are provided over active layer(s) 712 and gate layer 710, and device layer(s) 716 are provided over contact layer(s) 715 and second passive layer 714. Meanwhile, FIG. 8 illustrates a partial cross-sectional view of electronic device 300 in a gate contact build area of electronic device 300 after providing the semiconductor device layer(s) 708 over substrate assembly 307, according to the embodiment of FIG. 3. Here, first passivation layer 709 is provided over substrate assembly 307, gate layer 710 is provided over first passivation layer 709, first dielectric layer 711 is provided over gate layer 710, and second passivation layer 714 is provided over first dielectric layer 711, and contact layer(s) 715 are provided over gate layer 710. In these or other embodiments, semiconductor layer(s) 708 can be similar or identical to the semiconductor layer(s) of method 100 (FIG. 1). Accordingly, first passivation layer 709 can be similar or identical to the first passivation layer of activity 501 (FIG. 5), gate layer 710 can be similar or identical to the gate layer of activity 502 (FIG. 5), first dielectric layer 711 can be similar or identical to the first dielectric layer of activity 503 (FIG. 5), active layer(s) 712 can be similar or identical to the active layer(s) of activity 504 (FIG. 5), second dielectric layer 713 can be similar or identical to the second dielectric layer of activity 505 (FIG. 5), second passivation layer 714 can be similar or identical to the second passivation layer of activity 506 (FIG. 5), contact layer(s) 715 can be similar or identical to the contact layer(s) of activity 507 (FIG. 5), and device layer(s) 716 can be similar or identical to the device layer(s) of activity 508 (FIG. 5).

Turning now back to FIG. 4, the semiconductor device layer(s) can be provided (e.g., deposited) over part or substantially all of the second side of the device substrate. For example, in many embodiments, when the active sections of activity 104 (FIG. 1) are provided by removing (e.g., etching) excess active section material, the semiconductor device layer(s) can be provided (e.g., deposited) over substantially all of the second side of the device substrate. Alternatively, when the active sections of activity 104 (FIG. 1) are provided by selective deposition, the semiconductor device layer(s) can be provided (e.g., deposited) over only select parts of the second side of the device substrate.

Notably, whether the semiconductor device layer(s) are deposited over substantially all or only part of the second side of the device substrate, in many embodiments, a perimeter region of the second side of the device substrate can remain devoid of the semiconductor layer(s) to ensure that the material(s) provided for the semiconductor layers are not provided on the equipment handling the carrier substrate of method 100 (FIG. 1). The size (e.g., surface area, width, etc.) of the perimeter region can depend on the equipment and/or techniques used to provide the semiconductor device layer(s) over the second side of the device substrate. That is, the equipment and techniques can determine the accuracy of the deposition.

Meanwhile, when the active sections of activity 104 (FIG. 1) are provided by removing (e.g., etching) excess active section material, for reference purposes, the semiconductor device layer(s) can be said to comprise a first portion and a second portion. As explained in greater detail as follows, the first portion of the semiconductor layer(s) can represent the portion of the semiconductor layer(s) that is partially or completely removed, and the second portion of the semiconductor layer(s) can represent the portion of the semiconductor layer(s) that remain as part of the active sections of activity 104 of method 100 (FIG. 1).

Accordingly, activity 104 can comprise activity 402 of removing (e.g., etching) part or all of the first portion of the semiconductor device layer(s) from over the second side of the device substrate and leaving the second portion of the semiconductor device layer(s) remaining over the second side of the device substrate such that the active sections comprise the second portion of the semiconductor device layer(s). In some embodiments, activity 402 can be performed as one or more removal (e.g., etching) activities to remove the part or the all of the first portion of the semiconductor device layer(s). When activity 402 is implemented with one or more etching activities, in many embodiments, at least one of the one or more etching activities can be a timed etch.

For example, in many embodiments, activity 402 can comprise an activity of plasma etching the part or the all of the first portion of the semiconductor device layer(s) and/or an activity of wet etching the part or the all of the first portion of the semiconductor device layer(s). In these or other embodiments, the plasma etching can be fluorine based and/or the wet etching can be hydrofluoric-acid based. In many embodiments, the plasma etching activity can be performed before the wet etching activity. Further, the plasma etch activity can be timed and/or can anisotropically remove most of the part or the all of the first portion of the semiconductor device layer(s), and/or the wet etch activity can be shorter in time than the plasma etch activity and/or can be configured to remove the part or the all of the first portion of the semiconductor device layer(s) faster (e.g., substantially faster) than it removes the device substrate (e.g., to prevent the device substrate from being removed while ensuring the desired part or all of the first portion of the semiconductor device layer(s) is removed).

In many embodiments, the first portion of the semiconductor device layer(s) can occupy a first volume and the second portion of the semiconductor device layer(s) can occupy a second volume over the second side of the device substrate. The first volume and the second volume can be related in a volumetric ratio. In many embodiments, the volumetric ratio of the first volume to the second volume can be less than or equal to approximately 0.9. Further, in these or other embodiments, the volumetric ratio of the first volume to the second volume can be greater than or equal to approximately 0.005, 0.01, 0.02, 0.05, 0.08, and/or 0.1.

Further, activity 104 can comprise activity 403 of forming (e.g., etching) one or more interconnect vias over the contact layer(s). In some embodiments, activity 403 can be performed as one or more removal (e.g., etching) activities to form the interconnect via(s) over the contact layer(s). For example, in some embodiments, the interconnect via(s) can be formed through the device layer(s), thereby exposing a surface of the top most contact layer(s). When the interconnect via(s) are formed by etching (e.g., anisotropic etching), in many embodiments, the etch can be performed using a plasma etchant (e.g., a fluorine-based plasma etchant) or a wet etchant. In some embodiments, activity 403 can be performed as part of activity 402, and vice versa. In further embodiments, activity 402 and activity 403 can be performed approximately simultaneously, or sequentially, as desirable.

Returning now to FIG. 1, in many embodiments, method 100 can comprise activity 105 of providing one or more interconnects over the second side of the device substrate to electrically couple together the active sections. The interconnect(s) each can comprise a conductive material. For example, the conductive material can comprise metal (e.g., cracked gold). In these or other embodiments, the interconnect(s) each can comprise a wavy architecture (e.g., a spring-like architecture), such as, for example, with respect to a plane approximately parallel to the x-y plane of the device substrate and/or with respect to a plane approximately perpendicular to the x-y plane of the device substrate.

In these or other embodiments, the interconnect(s) can be configured to be reversibly expanded and/or contracted, such as, for example, when the electronic device is deformed and/or when the device substrate is decoupled from the carrier substrate, as discussed below. Accordingly, unlike straight metal interconnect(s), which may break when stretched and/or compressed, such wavy metal interconnects can electrically couple the active sections together while also permitting the electronic device to deform (e.g., flex and/or stretch). Generally, providing the wavy architecture parallel to the x-y plane of the device substrate can permit deformation of the electronic device of a type corresponding to a bowing and/or distortion of the device substrate, and providing the wavy architecture perpendicular to the x-y plane of the device substrate can permit deformation of the electronic device of a type corresponding to a bowing and/or warping of the device substrate, as these concepts are described above.

Exemplary wave architectures can comprise any suitable wave form (e.g., a curved wave form, such as, for example, a sinusoidal wave form, a triangular wave form, a saw tooth wave form, a square wave form, etc.). Further, curved wave forms can comprise any suitable amount of curvature. Further still, the wave architectures can have a constant or non-constant wave pattern, and/or the interconnects can have the same or different wave architectures as each other when multiple interconnects are implemented.

Figure 9:
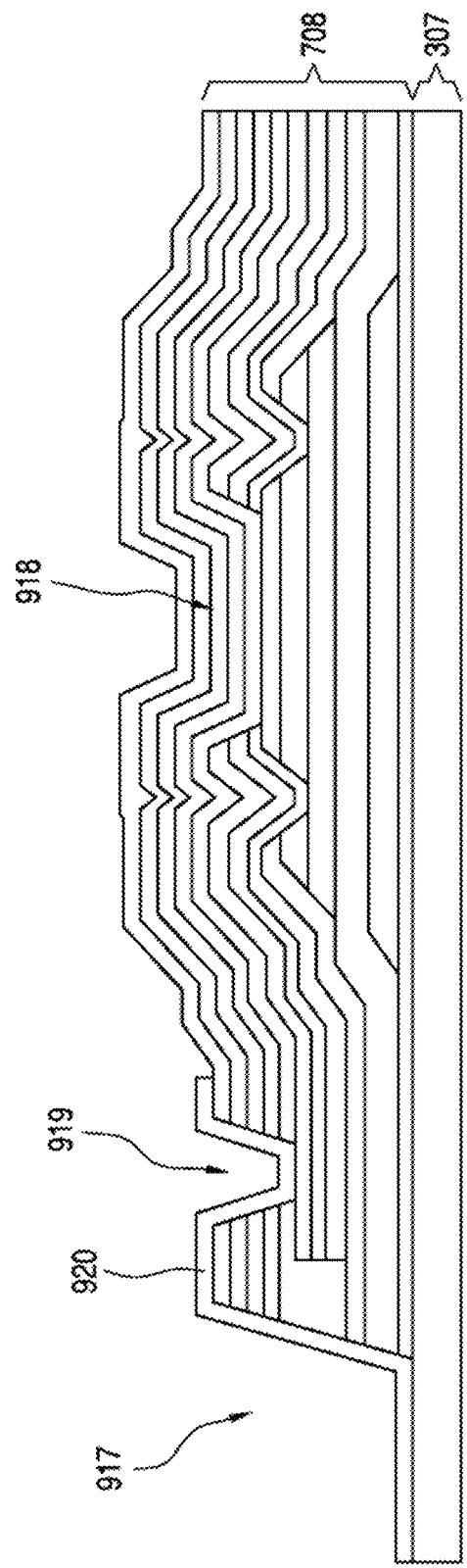
FIG. 9 illustrates a partial cross-sectional view of the electronic device of FIG. 3 in the device build area of the electronic device after removing (e.g., etching) all of a first portion of semiconductor device layer(s) from over the substrate assembly and leaving a second portion of the semiconductor device layer(s) remaining over the substrate assembly, after forming an interconnect via, and after providing an interconnect over the substrate assembly.

Turning ahead in the drawings, FIG. 9 illustrates a partial cross-sectional view of electronic device 300 in the device build area of electronic device 300 after removing (e.g., etching) all of a first portion 917 of semiconductor device layer(s) 708 from over substrate assembly 307 and leaving a second portion 918 of semiconductor device layer(s) 708 remaining over substrate assembly 307, after forming an interconnect via 919, and after providing interconnect 920 over substrate assembly 307. In these or other embodiments, first portion 917 can be similar or identical to the first portion of the semiconductor device layer(s) of activity 401 (FIG. 4), second portion 918 can be similar or identical to the second portion of activity 401 (FIG. 4), and interconnect 919 can be similar or identical to the interconnect(s) of method 100 (FIG. 1).

Returning again to FIG. 1, in some embodiments, method 100 can comprise activity 106 of providing a sacrificial layer over the second side of the device substrate and the active sections. In some embodiments, activity 106 can comprise an activity of coupling (e.g., removably coupling) the sacrificial layer to the second side of the device substrate and the active sections. In further embodiments, such as, for example, when activity 109 (below) is performed, activity 106 can comprise an activity of coupling (e.g., removably coupling) the sacrificial layer to the second elastomeric layer of activity 109.

In general, activity 106 can be performed after activities 101-105. In some embodiments, the sacrificial layer can be similar to a backing strip on an adhesive bandage. Accordingly, in many embodiments, the sacrificial layer can be selectively removed (e.g., peeled) from the electronic device when a user is ready to deploy the electronic device.

In these or other embodiments, the sacrificial layer can support the device substrate both while and after activity 107 is performed. The sacrificial layer can permit the electronic device to be more easily coupled to the surface of an object (e.g., organic tissue, consumables, etc.) without damaging the electronic device or crumpling the electronic device. Still, in some embodiments, activity 106 can be omitted.

In many embodiments, method 100 can comprise activity 107 of decoupling (e.g., debonding) the device substrate and the active sections from the carrier substrate. In some embodiments, when activity 106 is performed, activity 107 can be performed after activity 106. Meanwhile, as explained in greater detail below, when activity 108 (below) is performed, activity 107 can be performed before activity 108, and when activity 109 (below) is performed, activity 107 can be performed after activity 109.

For example, in some embodiments, performing activity 107 can comprise an activity of applying a release force (e.g., a steady release force) to the device substrate to decouple the device substrate and the active sections from the carrier substrate. In many embodiments, the release force can be applied to the device substrate (e.g., by hand). In these or other embodiments, the release force can be applied (or augmented) by inserting a blade under the device substrate and pressing on the device substrate in a direction away from the carrier substrate.

Further, in these or other embodiments, activity 107 can comprise an activity of severing the device substrate from the carrier substrate, such as, for example, using any suitable cutting implement (e.g., a blade, a laser, etc.). The activity of severing the device substrate from the carrier substrate can be performed alternatively to or as part of the activity of applying the release force to the device substrate.

In many embodiments, maintaining an angle of less than or equal to approximately 45 degrees between the device substrate and the carrier substrate when performing activity 107 can mitigate or prevent damage to the active section(s).

In some embodiments, activity 107 can be performed without first lowering the device substrate-carrier substrate coupling strength, such as, for example, using chemical or optical decoupling procedures (e.g., electronics on plastic by laser release (EPLaR™), surface free technology by laser annealing/ablation (SUFTLA™), etc.). In these embodiments, by avoiding using chemical or optical decoupling procedures (e.g., electronics on plastic by laser release (EPLaR™) surface free technology by laser annealing/ablation (SUFTLA™), etc.), device defects of the semiconductor device layer(s) and/or decreased semiconductor device yield that can result from using such chemical or optical debonding procedures can be reduced or eliminated. For example, optical decoupling procedures can damage the semiconductor device layer(s) through heat distortion and/or formation of particulate debris. Meanwhile, chemical decoupling procedures can damage the semiconductor device layer(s) by exposing the semiconductor device layer(s) to the chemical(s), resulting in degradation of the semiconductor device layer(s). Moreover, using chemical debonding procedures may require subsequent cleaning to remove any residual chemicals from the semiconductor device layer(s) and/or may not permit the device substrate to be kept approximately flat during decoupling because physically constraining the device substrate while immersing the device substrate in chemicals can be challenging. However, in other embodiments, the device substrate-carrier substrate coupling strength can be lowered as part of activity 107, such as, for example, when activity 104 and/or activity 401 (FIG. 4) is performed using the EPLaR™ manufacturing techniques described above.

In some embodiments, method 100 can comprise activity 108 of providing a first elastomeric layer over the first side of the device substrate. In these or other embodiments, the first elastomeric layer can comprise an elastomeric material (e.g., polydimethylsiloxane (PDMS)). In some embodiments, performing activity 108 can comprise an activity of coupling the first elastomeric layer to the first side of the device substrate. In other embodiments, activity 108 can be omitted.

In some embodiments, method 100 can comprise activity 109 of providing a second elastomeric layer over the second side of the device substrate and the active sections. In these or other embodiments, the second elastomeric layer can comprise the elastomeric material (e.g., PDMS). In some embodiments, performing activity 109 can comprise an activity of coupling the second elastomeric layer to the second side of the device substrate. In other embodiments, activity 109 can be omitted.

Implementing the electronic device of method 100 with the first elastomeric layer of activity 108 and/or the second elastomeric layer of activity 109 can increase the stretchability of the electronic device. In many embodiments, activity 108 and/or activity 109 are performed after activities 101-105 because the elastomeric material (e.g., PDMS) may not be able to withstand the manufacturing conditions of activities 101-105. For example, PDMS, which has a maximum processing temperature of approximately 100° C., cannot withstand conventional manufacturing conditions for flat panel electronic displays, which may include temperatures exceeding approximately 300° C. to approximately 350° C. and may include corrosive chemicals.

In various embodiments, method 100 can comprise activity 110 of providing an adhesive layer over one of the first side of the device substrate, the second side of the device substrate, the first elastomeric layer, or the second elastomeric layer. The adhesive layer can comprise a temporary medical adhesive and can be configured to aid in coupling the electronic device to an object (e.g., organic tissue, etc.), such as, for example, when electronic device is implemented as a smart bandage. Activity 110 can be performed before activity 106, before or after activity 108, and/or before or after activity 109, as applicable. In other embodiments, activity 110 can be omitted.

In some embodiments, method 100 can comprise an activity of rolling the device substrate through a roll-to-roll printing and coating device. In these embodiments, one or more of activities 101, 103, and 107 can be omitted. Further, one or more of activities 104-106 and 108-110 can be performed approximately simultaneously with the activity of rolling the device substrate through the roll-to-roll printing and coating device. Meanwhile, activity 102 can be performed prior to the activity of rolling the device substrate through the roll-to-roll printing and coating device. In these or other embodiments, any suitable roll-to-roll printing and coating device can be implemented.

Figure 10:
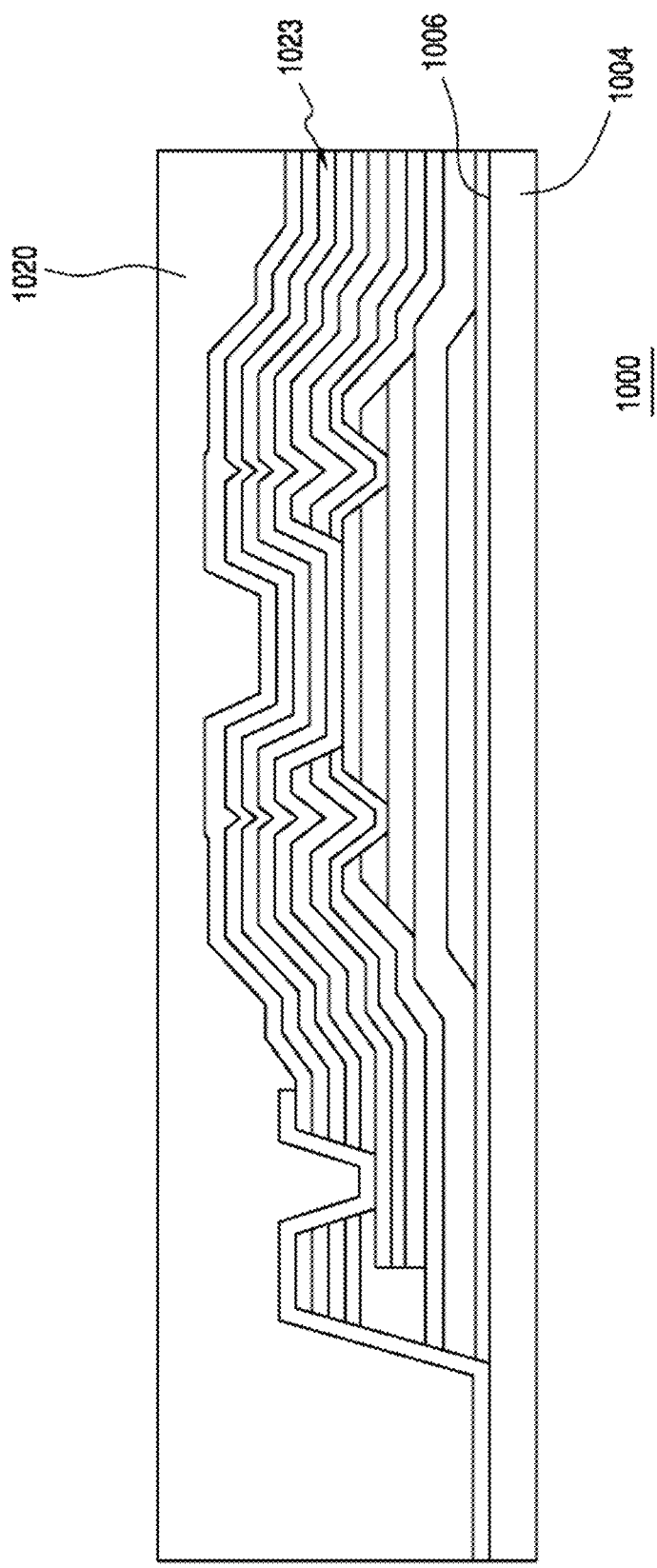
FIG. 10 illustrates a partial cross-sectional view of an electronic device in a device build area of the electronic device with a sacrificial layer of the electronic device coupled to a second side of a device substrate of the electronic device, according to an embodiment.

Turning ahead now in the drawings, FIG. 10 illustrates a partial cross-sectional view of an electronic device 1000 in a device build area of electronic device 1000 with a sacrificial layer 1020 of electronic device 1000 coupled to a second side 1006 of a device substrate 1004 of electronic device 1000 and an active section 1023 of electronic device 1000, according to an embodiment. Electronic device 1000 can be similar or identical to electronic device 300 (FIGS. 3, 6, 7, & 9). Sacrificial layer 1020 can be similar or identical to the sacrificial layer described above with respect to activity 106 (FIG. 1). Further, device substrate 1004 can be similar or identical to device substrate 304 (FIG. 3) and/or the device substrate described above with respect to activity 101 (FIG. 1); and second side 1006 can be similar or identical to second side 306 and/or the second side of the device substrate described above with respect to method 100 (FIG. 1). Also, active section 1023 can be similar or identical to one of the active sections described above with respect to method 100 (FIG. 1).

Figure 11:
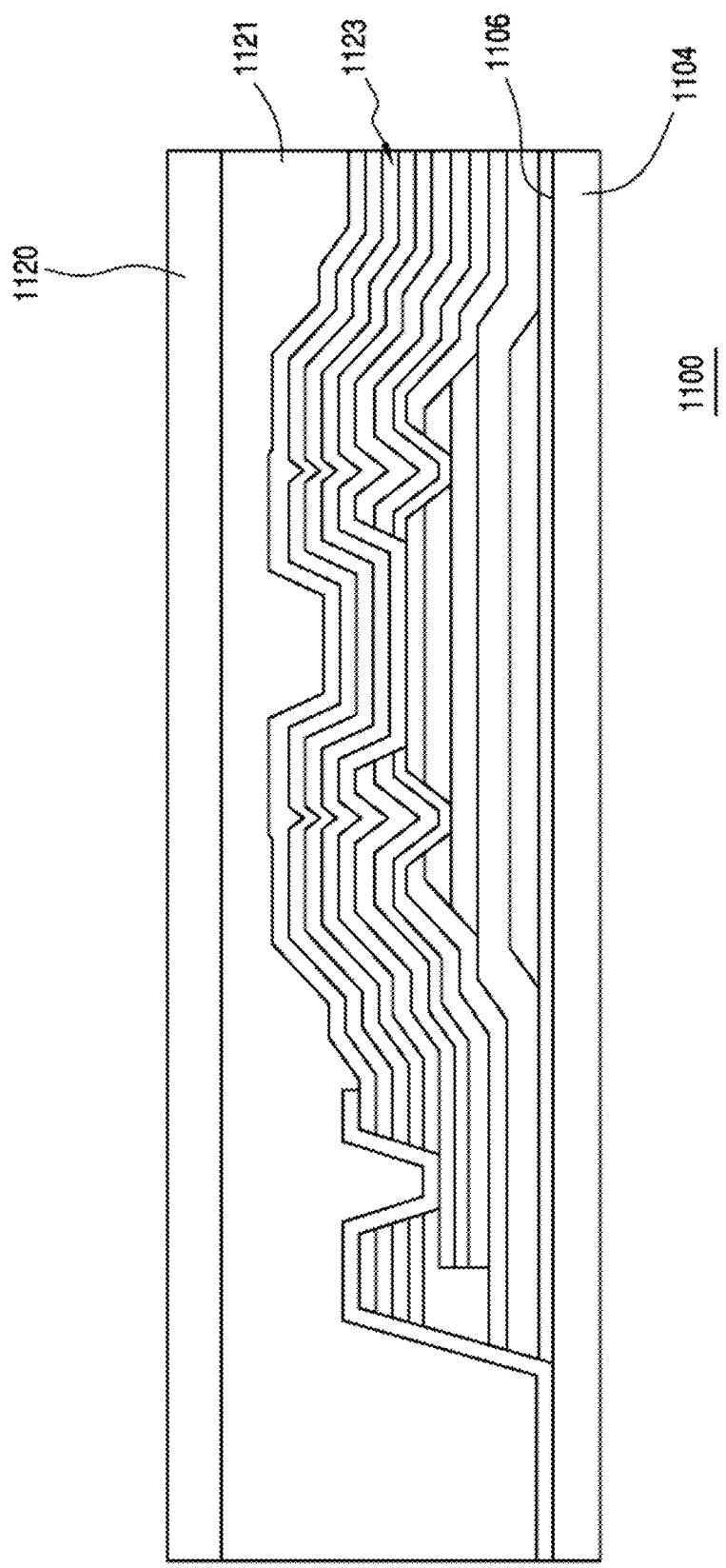
FIG. 11 illustrates a partial cross-sectional view of an electronic device in a device build area of the electronic device with an elastomeric layer of the electronic device coupled to a second side of a device substrate of the electronic device and a sacrificial layer of the electronic device coupled to the elastomeric layer, according to an embodiment.

Meanwhile, FIG. 11 illustrates a partial cross-sectional view of an electronic device 1100 in a device build area of electronic device 1100 with an elastomeric layer 1121 of electronic device 1100 coupled to a second side 1106 of a device substrate 1104 of electronic device 1100 and an active section 1123 of electronic device 1100, and a sacrificial layer 1120 of electronic device 1000 coupled to elastomeric layer 1121, according to an embodiment. Electronic device 1100 can be similar or identical to electronic device 300 (FIGS. 3, 6, 7, & 9) and/or electronic device 1000 (FIG. 10). Sacrificial layer 1120 can be similar or identical to the sacrificial layer described above with respect to activity 106 (FIG. 1) and/or sacrificial layer 1020 (FIG. 10). Elastomeric layer 1121 can be similar or identical to the second elastomeric layer described above with respect to activity 108 (FIG. 1). Further, device substrate 1004 can be similar or identical to device substrate 304 (FIG. 3), device substrate 1004 (FIG. 10), and/or the device substrate described above with respect to activity 101 (FIG. 1); and second side 1006 can be similar or identical to second side 306, second side 1006 (FIG. 10) and/or the second side of the device substrate described above with respect to method 100 (FIG. 1). Also, active section 1123 can be similar or identical to one of the active sections described above with respect to method 100 (FIG. 1) and/or active section 1023 (FIG. 10).

Figure 12:
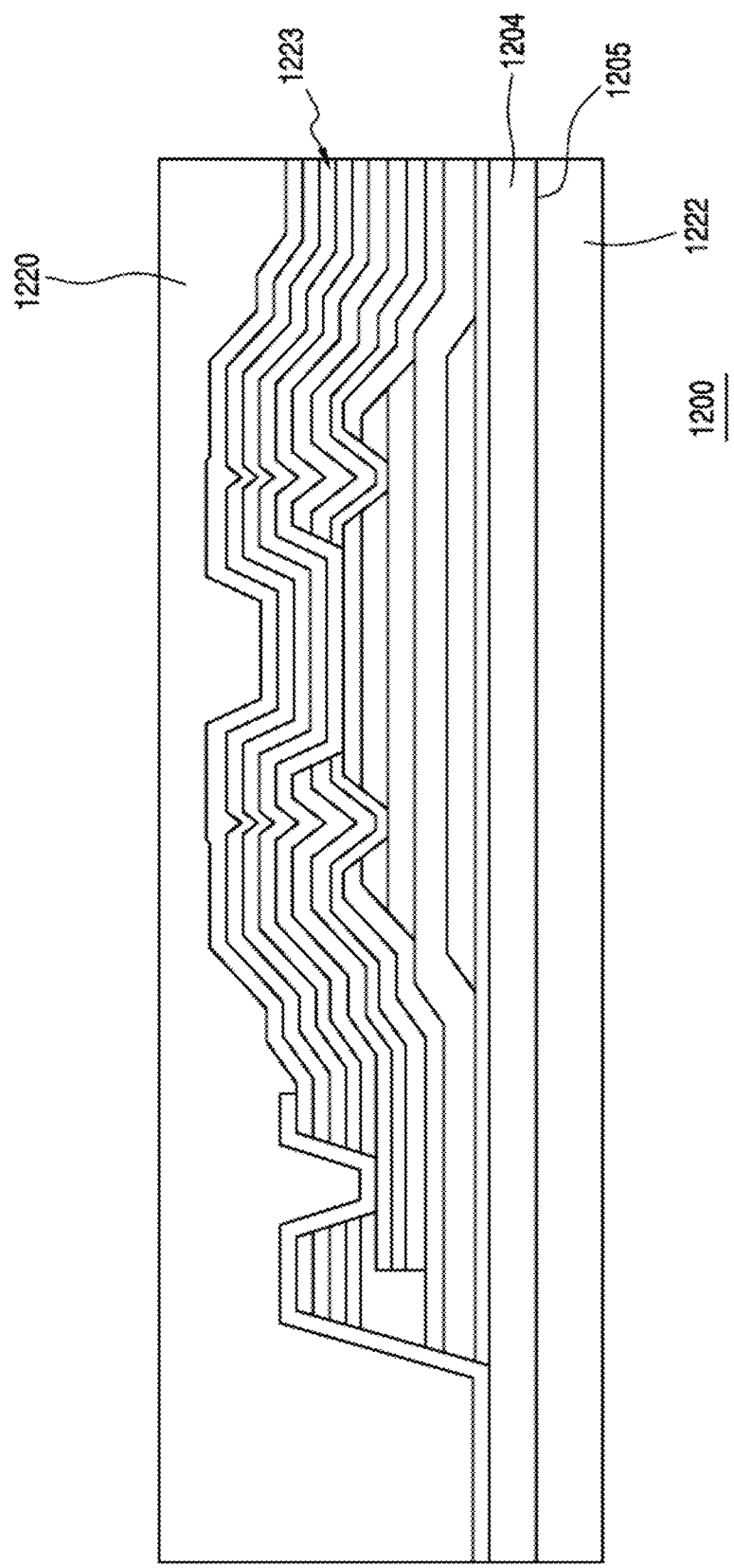
FIG. 12 illustrates a partial cross-sectional view of an electronic device in a device build area of the electronic device with an elastomeric layer of the electronic device coupled to a first side of a device substrate of the electronic device and a sacrificial layer of the electronic device coupled to a second side of the device substrate, according to an embodiment.

Further, FIG. 12 illustrates a partial cross-sectional view of an electronic device 1200 in a device build area of electronic device 1200 with an elastomeric layer 1222 of electronic device 1200 coupled to a first side 1205 of a device substrate 1204 of electronic device 1200 and a sacrificial layer 1220 of electronic device 1200 coupled to a second side 1206 of device substrate 1204 and an active section 1223 of electronic device 1200, according to an embodiment. Electronic device 1200 can be similar or identical to electronic device 300 (FIGS. 3, 6, 7, & 9), electronic device 1000 (FIG. 10) and/or electronic device 1100 (FIG. 11). Sacrificial layer 1220 can be similar or identical to the sacrificial layer described above with respect to activity 106 (FIG. 1), sacrificial layer 1020 (FIG. 10) and/or sacrificial layer 1120 (FIG. 11). Elastomeric layer 1222 can be similar or identical to the first elastomeric layer described above with respect to activity 108 (FIG. 1). Further, device substrate 1204 can be similar or identical to device substrate 304 (FIG. 3), device substrate 1004 (FIG. 10), device substrate 1104 (FIG. 11) and/or the device substrate described above with respect to activity 101 (FIG. 1); second side 1006 can be similar or identical to second side 306, second side 1006 (FIG. 10), second side 1106 (FIG. 11), and/or the second side of the device substrate described above with respect to method 100 (FIG. 1); and first side 1205 can be similar or identical to first side 305 (FIG. 3) and/or the first side of the device substrate described above with respect to method 100 (FIG. 1). Also, active section 1223 can be similar or identical to one of the active sections described above with respect to method 100 (FIG. 1), active section 1023 (FIG. 10), and/or active section 1123 (FIG. 11).

Figure 13:
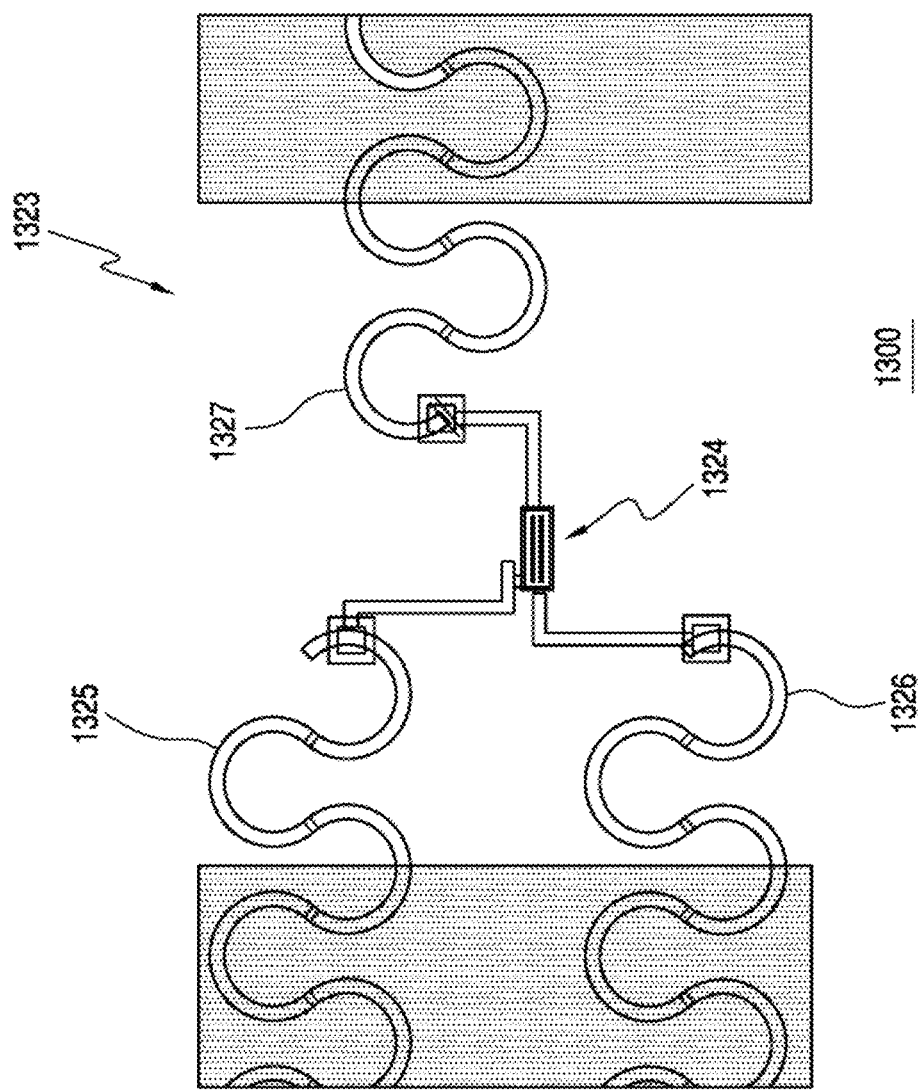
FIG. 13 illustrates a partial top view of an electronic device including an active section having a semiconductor device coupled to three interconnects, according to an embodiment.

Further still, FIG. 13 illustrates a partial top view of an electronic device 1300 including an active section 1323 having a semiconductor device 1324 coupled to interconnect 1325, interconnect 1326, and interconnect 1327, according to an embodiment. Electronic device 1300 can be similar or identical to electronic device 300 (FIGS. 3, 6, 7, & 9), electronic device 1000 (FIG. 10), electronic device 1100 (FIG. 11), and/or electronic device 1200 (FIG. 12). Semiconductor device 1324 can be similar or identical to the semiconductor device(s) described above with respect to method 100 (FIG. 1), and interconnects 1325-1327 each can be similar or identical to the interconnect(s) described above with respect to method 100 (FIG. 1), interconnect 919 (FIG. 9), and/or interconnect 920 (FIG. 9). Also, active section 1323 can be similar or identical to one of the active sections described above with respect to method 100 (FIG. 1), active section 1023 (FIG. 10), active section 1123 (FIG. 11), and/or active section 1223 (FIG. 12).

Figure 14:
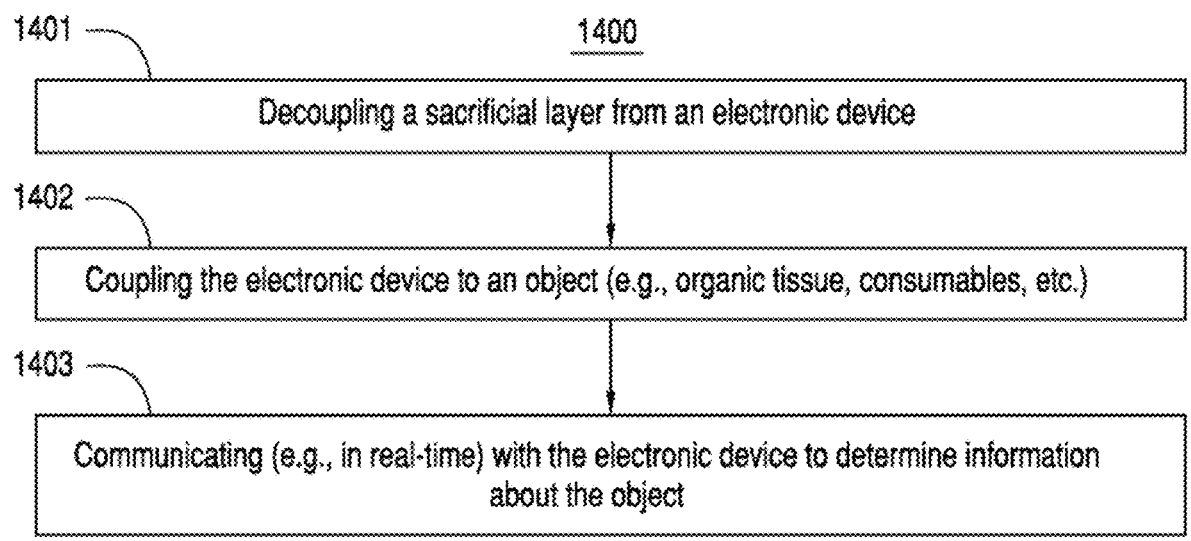
FIG. 14 illustrates an example of a method, according to an embodiment.

Turning ahead in the drawings, FIG. 14 illustrates an example of a method 1400, according to an embodiment. Method 1400 is merely exemplary and is not limited to the embodiments presented herein. Method 1400 can be employed in many different embodiments or examples not specifically depicted or described herein. In some embodiments, the activities of method 1400 can be performed in the order presented. In other embodiments, the activities of method 1400 can be performed in any other suitable order. In still other embodiments, one or more of the activities in method 1400 can be combined or skipped.

Method 1400 can comprise activity 1401 of decoupling a sacrificial layer from an electronic device. The electronic device can be similar or identical to electronic device 300 (FIGS. 3, 6, 7, & 9), electronic device 1000 (FIG. 10), electronic device 1100 (FIG. 11), electronic device 1200 (FIG. 12), and/or electronic device 1300 (FIG. 13). Further, the sacrificial layer can be similar or identical to the sacrificial layer described above with respect to activity 106 (FIG. 1), sacrificial layer 1020 (FIG. 10), sacrificial layer 1120 (FIG. 11), and/or sacrificial layer 1220 (FIG. 12). In some embodiments, activity 1401 can be omitted.

Further, method 1400 can comprise activity 1402 of coupling the electronic device to an object (e.g., organic tissue, consumables, etc.). In many embodiments, activity 1402 can be performed after activity 1401.

Further still, method 1400 can comprise activity 1403 of communicating (e.g., in real-time) with the electronic device to determine information about the object. In some embodiments, activity 1403 can be performed while the electronic device is coupled to the object. In many embodiments, when the object is organic tissue, activity 1403 can be performed to detect and/or diagnose multiple diseases of an organism having the organic tissue with clinical level sensitivity. In various embodiments, activity 1403 can be performed using any suitable mechanisms (e.g., a computer, an antenna, etc.) and medium (e.g., Bluetooth, Near Field Communication, Wi-Fi, a cable, a bus, etc.) for communication (e.g., wired or wireless communication) with the electronic device.

Figures 15, 16:
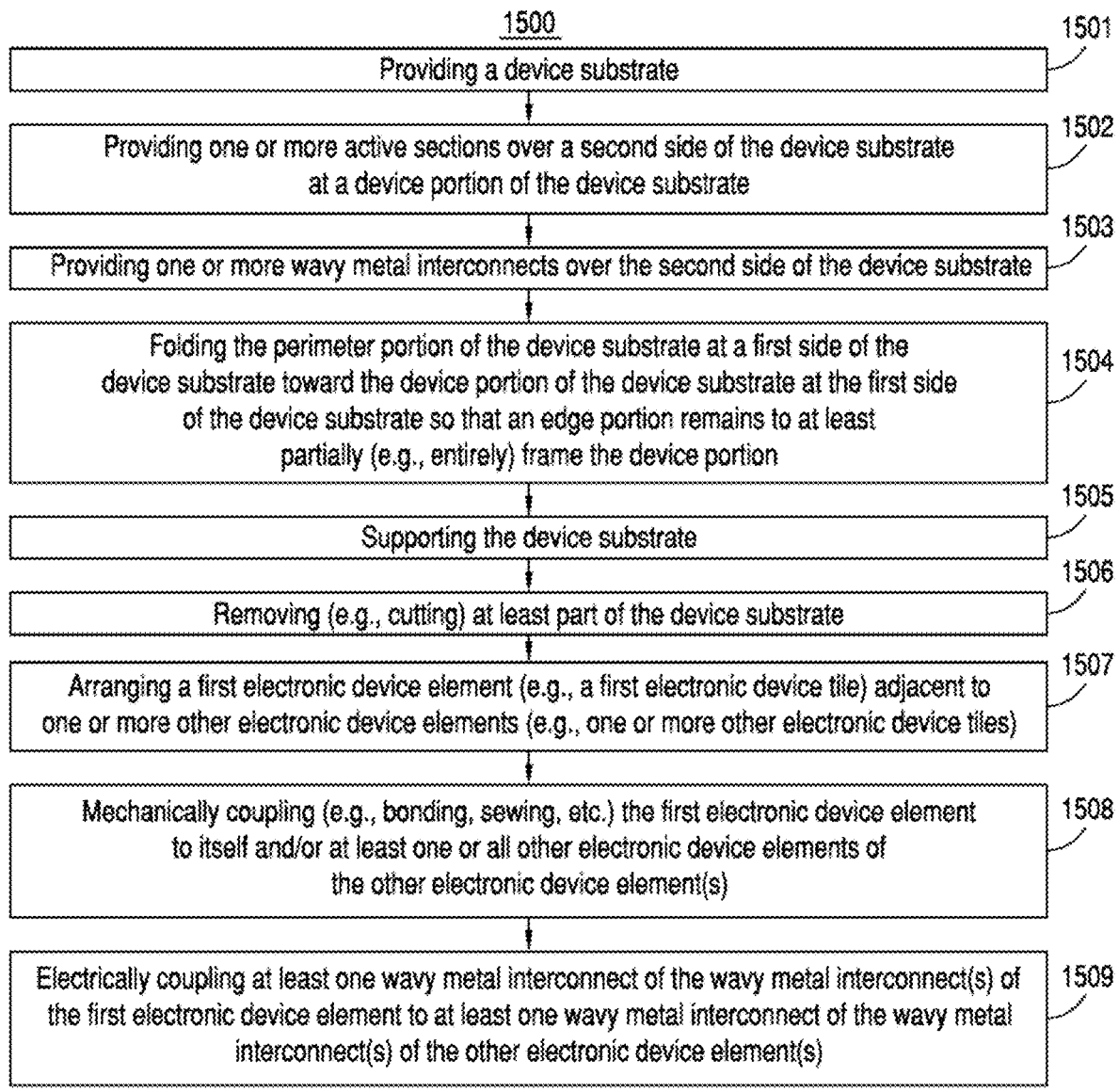
FIG. 15 illustrates an example of a method of providing an electronic device, according to an embodiment.
FIG. 16 illustrates an exemplary activity of folding a perimeter portion of a device substrate of the electronic device at the first side of the device substrate toward a device portion of the device substrate at the first side of the device substrate so that an edge portion remains to at least partially (e.g., entirely) frame the device portion, according to the embodiment of FIG. 15.

Turning ahead in the drawings, FIG. 15 illustrates an example of a method 1500 of providing an electronic device, according to an embodiment. Method 1500 is merely exemplary and is not limited to the embodiments presented herein. Method 1500 can be employed in many different embodiments or examples not specifically depicted or described herein. In some embodiments, the activities of method 1500 can be performed in the order presented. In other embodiments, the activities of method 1500 can be performed in any other suitable order. In still other embodiments, one or more of the activities in method 1500 can be combined or skipped.

The electronic device can comprise any suitable electronic device. For example, in many embodiments, the electronic device can comprise one or more flat panel electronic displays, one or more active matrix arrays of an imaging system (e.g., one or more active matrix arrays of an x-ray imaging system), etc.

Further, in these or other embodiments, the electronic device can be similar or identical to the electronic device described above with respect to method 100 (FIG. 1) and/or to electronic device 300 (FIGS. 3, 6, 7, & 9). Accordingly, in some embodiments, the electronic device can comprise a deformable electronic device. For example, in many embodiments, the electronic device can be flexible and/or stretchable. As discussed in greater detail herein, the flexibility and/or stretchability of the electronic device can depend on the material properties and/or the thickness dimension of the device substrate and/or the support structure implemented with the electronic device.

Method 1500 comprises activity 1501 of providing a device substrate. The device substrate can be similar or identical to the device substrate described above with respect to method 100 (FIG. 1) and/or to device substrate 304 (FIG. 3). For example, the device substrate can comprise a first side and a second side opposite the first side. The first side of the device substrate can be similar or identical to the first side of the device substrate described above with respect to method 100 (FIG. 1) and/or to first side 305 (FIG. 3); and/or the second side of the device substrate can be similar or identical to the second side of the device substrate described above with respect to method 100 (FIG. 1) and/or to second side 306 (FIG. 3).

In many embodiments, the device substrate can comprise a device portion and a perimeter portion. The perimeter portion can at least partially (e.g., entirely) frame the device portion such that the perimeter portion at least partially (e.g., entirely) borders the device portion. In particular, the perimeter portion can at least partially (e.g., entirely) frame the device portion in the x-y plane and/or median plane of the device substrate when the device substrate is in a relaxed (e.g., non-deformed) state.

In some embodiments, the device substrate and/or the device portion of the device substrate can comprise an approximately rectangular shape, such as, for example, in the x-y plane and/or median plane of the device substrate when the device substrate is in a relaxed (e.g., non-deformed) state. Further, in some of these embodiments, the device substrate and/or the device portion of the device substrate can comprise an approximately square shape, such as, for example, in the x-y plane and/or median plane of the device substrate when the device substrate is in a relaxed (e.g., non-deformed) state.

Method 1500 can comprise activity 1502 of providing one or more active sections over the second side of the device substrate at the device portion. Activity 1502 can be performed after activity 1501 or approximately simultaneously with activity 1501.

The active section(s) can be similar or identical to the active section(s) described above with respect to method 100 (FIG. 1). Accordingly, the active section(s) each can comprise one or more semiconductor device(s). For example, the semiconductor device(s) can comprise one or more detector semiconductor devices (e.g., one or more photodiodes), one or more emitter semiconductor devices (e.g., one or more light emitting diodes), or a combination of both. In some embodiments, the perimeter portion is devoid of the active section(s).

In many embodiments, the semiconductor device(s) each can comprise one or more picture elements (i.e., pixels). Depending on whether the semiconductor device(s) comprise detector semiconductor device(s) or emitter semiconductor device(s), the pixel(s) can comprise one or more detector pixels and/or one or more emitter pixels, as applicable. In these or other embodiments, the pixel(s) each can comprise a smallest cross dimension. The smallest cross dimension can refer to a distance measured in a plane approximately parallel to the x-y plane and/or the median plane of the device substrate when the device substrate is in a relaxed (e.g., non-deformed) state. In some embodiments, the smallest cross dimension of two or more pixels of a same semiconductor device or different semiconductor devices can be the same as each other, and in these or other embodiments, the smallest cross dimension of two or more of the pixels of a same semiconductor device or different semiconductor devices can be different from each other.

In other embodiments, the semiconductor device(s) can comprise any other electronic element or elements suitable for arrangement in an array like pixels of a pixel array. Accordingly, in these embodiments, as similarly discussed with respect to the pixel(s) above, the other electronic element(s) each can comprise a smallest cross dimension similar to the smallest cross dimension(s) of the pixel(s).

Method 1500 can comprise activity 1503 of providing one or more wavy metal interconnects over the second side of the device substrate, such as, for example, at the device portion of the device substrate, and in many embodiments, at the perimeter portion of the device substrate. The wavy metal interconnect(s) can be similar or identical to the interconnect(s) described above with respect to method 100 (FIG. 1), to interconnect 919 (FIG. 9), to interconnect 920 (FIG. 9), and/or to one or more of interconnects 1325-1327 (FIG. 13). In various embodiments, activity 1503 can be performed approximately simultaneously with at least part of activity 1502.

Figure 20:
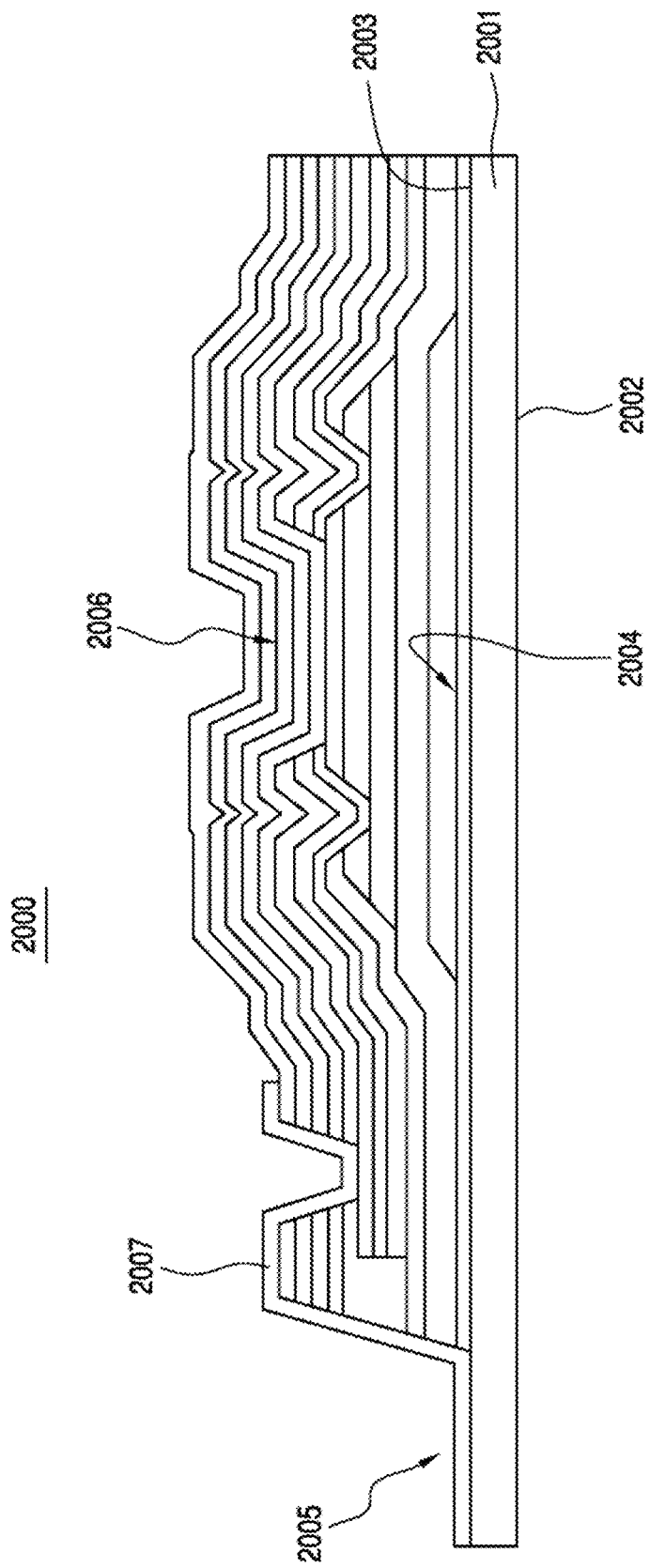
FIG. 20 illustrates a partial cross-sectional view of an electronic device, according to an embodiment.

Turning ahead in the drawings, FIG. 20 illustrates a partial cross-sectional view of electronic device 2000, according to an embodiment. In these embodiments, electronic device 2000 can be similar or identical to the electronic device of method 1500 (FIG. 15), such as, for example, after providing the device substrate, after providing the active section(s) over the second side of the device substrate at the device portion, and after providing the wavy metal interconnect(s) over the second side of the device substrate, according to the method of FIG. 15. Accordingly, electronic device 2000 can comprise device substrate 2001. Meanwhile, device substrate 2001 can comprise first side 2002, second side 2003, device portion 2004, and perimeter portion 2005. Further, electronic device 2000 can comprise active section 2006 and wavy metal interconnect 2007. In these or other embodiments, device substrate 2001 can be similar or identical to the device substrate described above with respect to method 1500 (FIG. 15); first side 2002 can be similar or identical to the first side of the device substrate described above with respect to method 1500 (FIG. 15); second side 2003 can be similar or identical to the second side of the device substrate described above with respect to method 1500 (FIG. 15); device portion 2004 can be similar or identical to the device portion of the device substrate described above with respect to method 1500 (FIG. 15); perimeter portion 2005 can be similar or identical to the perimeter portion of the device substrate described above with respect to method 1500 (FIG. 15); active section 2006 can be similar or identical to one of the active section(s) described above with respect to method 1500 (FIG. 15); and/or wavy metal interconnect 2007 can be similar or identical to one of the wavy metal interconnect(s) described above with respect to method 1500 (FIG. 15).

Referring now back to FIG. 15, method 1500 can comprise activity 1504 of folding the perimeter portion of the device substrate at the first side of the device substrate toward the device portion of the device substrate at the first side of the device substrate so that an edge portion remains to at least partially (e.g., entirely) frame the device portion. That is, performing activity 1504 can comprise folding part (e.g., a majority) of the perimeter portion of the device substrate at the first side toward the device portion of the device substrate at the first side of the device substrate so that a remaining part of the perimeter portion of the device substrate (i.e., the edge portion) remains to at least partially (e.g., entirely) frame the device portion in the x-y plane and/or median plane of the device portion of the device substrate. In many embodiments, performing activity 1504 can have the effect of limiting a portion of the device substrate that remains approximately parallel to the x-y plane and/or the median plane of the device portion of the device substrate as much as possible to the device portion of the device substrate, subject to the deformability of the device substrate, active section(s), and/or wavy metal interconnect(s) implemented with the electronic device. The advantages of limiting the portion of the device substrate remaining in the x-y plane and/or the median plane of the device portion of the device substrate as much as possible to the device portion of the device substrate are explained in greater detail below. In many embodiments, activity 1504 can be performed after activities 1501-1503.

The edge portion can refer to a part of the perimeter portion of the device substrate directly adjacent to the device portion of device substrate and extending through at least part (e.g., half or all) of a curvature of the perimeter portion of the device substrate resulting from performing activity 1504. In some embodiments, the curvature can refer to a crease formed in the perimeter portion of the device substrate as a radius of the curvature of the perimeter portion approaches zero (e.g., when the perimeter portion is folded sharply). In many embodiments, the radius of the curvature can be dependent on the material properties and the thickness dimension of the device substrate. In these or other embodiments, it can be desirable to reduce the radius of curvature as much as possible to minimize the edge portion width dimension, as explained below.

As indicated above, the edge portion can comprise an edge portion width dimension. The edge portion width dimension can refer to a dimension of the edge portion measured from any point along an interface of the perimeter portion (e.g., edge portion) and the device portion of the device substrate in a direction approximately orthogonal to the interface and approximately parallel to the x-y plane and/or median plane of the device portion of the device substrate. In some embodiments, the edge portion width dimension can be approximately constant along at least part of the interface of the perimeter portion and the device portion of the device substrate, while in these or other embodiments, the edge portion width dimension can vary along at least part of the interface. Nonetheless, in many embodiments, the edge portion width dimension (e.g., at any point along the interface of the perimeter portion and the device portion of the device substrate) can be smaller than the smallest cross dimension of one or more (e.g., all) of the pixel(s) of the semiconductor device(s) of the active section(s) of the electronic device. Because the edge portion width dimension (e.g., at any point along the interface of the perimeter portion and the device portion of the device substrate) can be smaller than the smallest cross dimension of one or more (e.g., all) of the pixel(s) of the semiconductor device(s) of the active section(s) of the electronic device, the electronic device can be said to comprise a zero edge electronic device. The electronic device can be referred to as a zero edge electronic device because by having an edge portion width dimension (e.g., at any point along the interface of the perimeter portion and the device portion of the device substrate) that is smaller than the smallest cross dimension of one or more (e.g., all) of the pixel(s) of the semiconductor device(s) of the active section(s) of the electronic device, the edge portion of the electronic device can be effectively imperceptible to a human eye. In further embodiments, when the semiconductor device(s) comprise other electronic element(s) suitable for arrangement in an array like pixels of a pixel array, as provided for above, the edge portion width dimension (e.g., at any point along the interface of the perimeter portion and the device portion of the device substrate) can similarly be smaller than the smallest cross dimension of the other electronic element(s).

Notably, in many embodiments, performing activity 1502 and/or activity 1503 in accordance with the activities of method 100 (FIG. 1) can make it possible to perform activity 1504. For example, in these embodiments, performing activity 1502 and/or activity 1503 in accordance with the activities of method 100 (FIG. 1) can permit the device substrate to be folded without damaging the active section(s) and wavy metal interconnect(s) provided over the device substrate.

Turning ahead in the drawings, FIG. 16 illustrates an exemplary activity 1504, according to the embodiment of FIG. 15. For example, activity 1504 can comprise activity 1601 of folding the perimeter portion of the device substrate at the first side of the device substrate toward the device portion of the device substrate at the first side of the device substrate such that at least part of the perimeter portion (e.g., a portion of the perimeter portion excluding the edge portion) forms an angle with the device portion (e.g., at one or more points along the interface of the perimeter portion and the device portion of the device substrate). For example, the angle can be less than 180 degrees. In further examples, the angle can be less than or equal to approximately 90 degrees.

In these embodiments, as the angle formed between the perimeter portion and the device portion approaches approximately 90 or less degrees, the edge portion width dimension can approach and/or approximately comprise a same value as the thickness dimension of the device substrate. For example, the edge portion width dimension can comprise approximately 20 micrometers. Accordingly, like the edge portion width dimension, in many embodiments, the thickness dimension of the device substrate can be smaller than the smallest cross dimension of one or more (e.g., all) of the pixel(s) of the semiconductor device(s) of the active section(s) of the electronic device.

Figure 17:
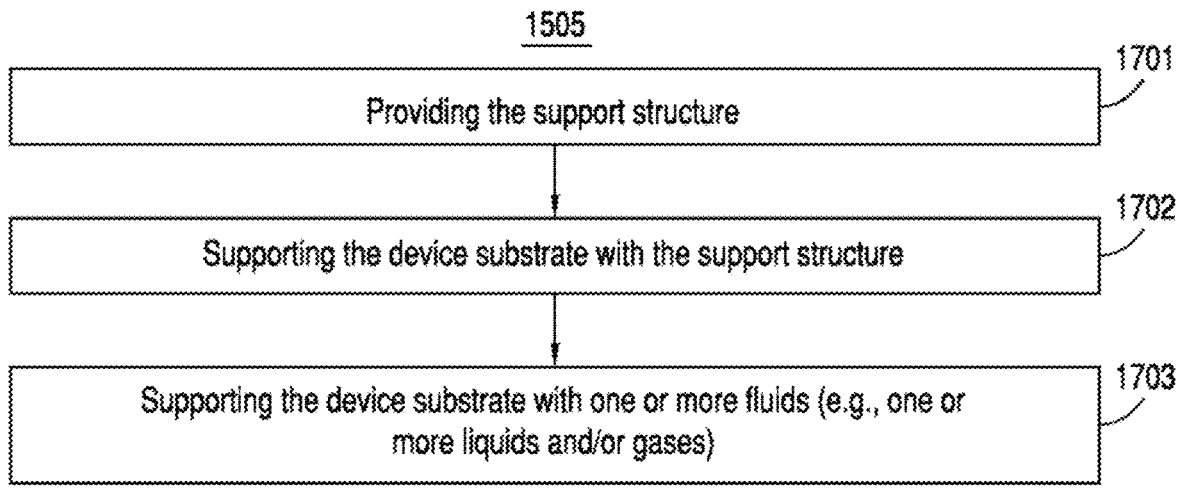
FIG. 17 illustrates an exemplary activity of supporting the device substrate of the electronic device, according to the embodiment of FIG. 15.

Returning now back to FIG. 15, method 1500 can comprise activity 1505 of supporting the device substrate. In many embodiments, activity 1505 can be performed after activities 1501-1503. Further, in these or other embodiments, activity 1505 can be performed before or approximately simultaneously with activity 1504. Meanwhile, when the device substrate is coupled to a carrier substrate to perform activity 1502 and/or activity 1503, as described above with respect to method 100 (FIG. 1), the device substrate can be decoupled from the carrier substrate before activity 1504 and/or activity 1505 are performed. FIG. 17 illustrates an exemplary activity 1505, according to the embodiment of FIG. 15.

For example, activity 1505 can comprise activity 1701 of providing a support structure. The support structure can be configured to reinforce the device substrate and/or active sections of the electronic device. Accordingly, the support structure can comprise any suitable material or materials being more rigid than the device substrate and/or active sections. Nonetheless, despite being more rigid than the device substrate and/or active sections, in many embodiments, the support structure can still be deformable (e.g., flexible and/or stretchable) to maintain the deformability of the electronic device. In many embodiments, the support structure can comprise a support layer, a support mesh or weave, one or more support poles, one or more hollow or solid bodies, etc.

Figure 18:
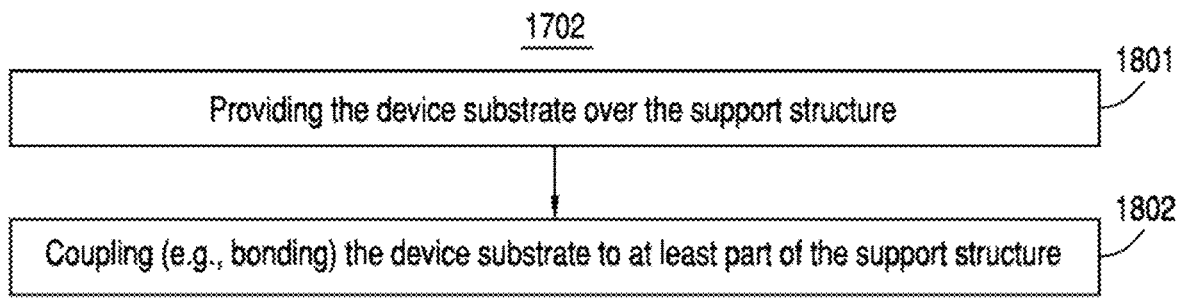
FIG. 18 illustrates an exemplary activity of supporting the device substrate of the electronic device with a support structure; according to the embodiment of FIG. 15.

Further, activity 1505 can comprise activity 1702 of supporting the device substrate with the support structure. FIG. 18 illustrates an exemplary activity 1702, according to the embodiment of FIG. 15.

For example, activity 1702 can comprise activity 1801 of providing the device substrate over the support structure. In some embodiments, activity 1801 can be omitted.

Further, activity 1702 can comprise activity 1802 of coupling (e.g., bonding) the device substrate to at least part of the support structure. In some embodiments, activity 1802 can be omitted. Further, in other embodiments, activity 1801 and activity 1802 can be performed approximately simultaneously.

Referring back to FIG. 17, in further embodiments, activity 1505 can comprise activity 1703 of supporting the device substrate with one or more fluids (e.g., one or more liquids and/or gases). For example, in these embodiments, the device substrate can be supported by gaseous air or gaseous helium. In some embodiments, activity 1701 and/or activity 1702 can be omitted when activity 1703 is performed, or vice versa.

Meanwhile, referring back to FIG. 16, in some embodiments, activity 1504 can comprise activity 1602 of folding the perimeter portion around the support structure (e.g., the support layer). In these embodiments, after performing activity 1602, at least part of the support structure can be disposed between the device portion of the device substrate and the perimeter portion of the device substrate. In some embodiments, activity 1602 can be omitted.

In some embodiments, the support structure of activity 1701 (FIG. 17) can comprise rounded corners to facilitate performance of activity 1602. That is, implementing the support structure with rounded corners can permit the perimeter portion to be positioned more closely to the support structure when the perimeter portion is folded around the support structure.

Figure 21:
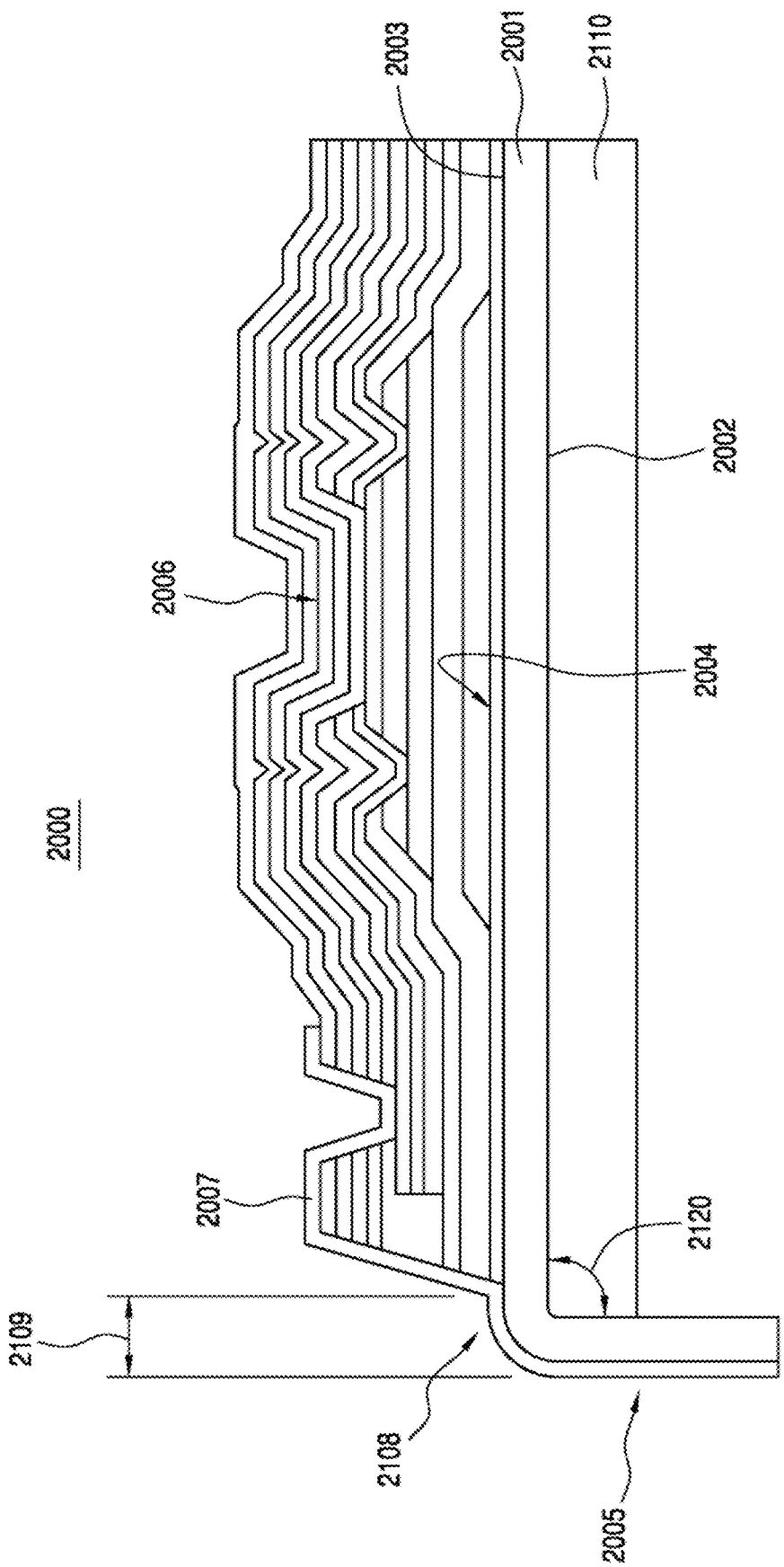
FIG. 21 illustrates another partial cross-sectional view of the electronic device, according to the embodiment of FIG. 20.

Turning ahead in the drawings, FIG. 21 illustrates another partial cross-sectional view of electronic device 2000, according to the embodiment of FIG. 20. In these embodiments, electronic device 2000 can be similar or identical to the electronic device of method 1500 (FIG. 15), such as, for example, after folding the perimeter portion of the device substrate at the first side of the device substrate toward the device portion of the device substrate at the first side of the device substrate so that an edge portion remains to at least partially (e.g., entirely) frame the device portion, and after supporting the device substrate with the support structure, according to the method of FIG. 15. Accordingly, electronic device 2000 can comprise edge portion 2108 and edge portion width dimension 2109. Further, device substrate 2001 can be located over support structure 2210 of electronic device 2000, and perimeter portion 2005 can form angle 2120 with device portion 2004. In many embodiments, edge portion 2108 can be similar or identical to the edge portion of the device substrate and/or perimeter portion of the device substrate of the electronic device described above with respect to method 1500 (FIG. 15); edge portion width dimension 2109 can be similar or identical to the edge portion width dimension described above with respect to method 1500 (FIG. 15); and/or support structure 2110 can be similar or identical to the support structure described above with respect to method 1500 (FIG. 15).

Figure 19:
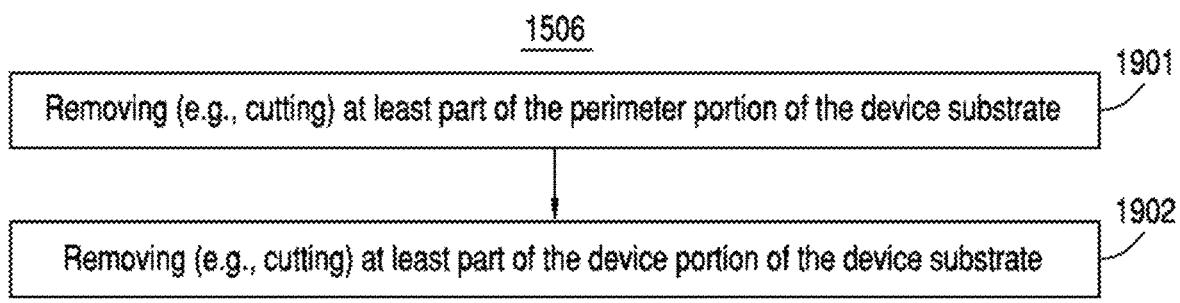
FIG. 19 illustrates an exemplary activity of cutting at least part of the device substrate of the electronic device, according to the embodiment of FIG. 15.

Now, referring back to FIG. 15, in many embodiments, method 1500 can comprise activity 1506 of removing (e.g., cutting) at least part of the device substrate. In some embodiments, activity 1506 can be omitted. FIG. 19 illustrates an exemplary activity 1506, according to the embodiment of FIG. 15.

For example, activity 1506 can comprise activity 1901 of removing (e.g., cutting) at least part of the perimeter portion of the device substrate. In these embodiments, activity 1901 can be performed before activity 1504. Further, in many embodiments, performing activity 1901 can facilitate performance of activity 1504. For example, in some embodiments, performing activity 1901 can comprise cutting the perimeter portion into two or more discrete flaps (e.g., similar to the flaps of a card board box) to facilitate performance of activity 1504. In particular, cutting the perimeter portion into the discrete flaps can prevent the perimeter portion of the device substrate from bunching up during or after performance of activity 1504, such as, for example, when performing activity 1504 involves folding the perimeter portion of the device substrate at the first side of the device substrate toward the device portion of the device substrate at the first side of the device substrate in multiple directions relative to the device portion of the device substrate. Still, in other embodiments, activity 1901 can be omitted, such as, for example, when performing activity 1504 involves folding the perimeter portion of the device substrate at the first side of the device substrate toward the device portion of the device substrate at the first side of the device substrate in only one direction relative to the device portion of the device substrate. Notably, preventing the perimeter portion from bunching up during or after performance of activity 1504 can tighten the curvature of the perimeter portion that results from performing activity 1504 and/or minimize the edge portion width dimension of the edge portion that result from performing activity 1504.

Further, activity 1506 can comprise activity 1902 of removing (e.g., cutting) at least part of the device portion of the device substrate. For example, at least part of the device portion of the device substrate can be removed (e.g., cut) so that the device portion of the device better conforms to one or more surfaces of the support structure implemented to support the device substrate at activity 1702 (FIG. 17). Accordingly, in many embodiments, activity 1902 can be performed when activity 1505 (FIG. 15) comprises activity 1702 (FIG. 17). Moreover, activity 1902 can be performed prior to activity 1505 (FIG. 15). In some embodiments, at least part of activity 1902 can be performed approximately simultaneously with activity 1901, and vice versa.

Figure 23:
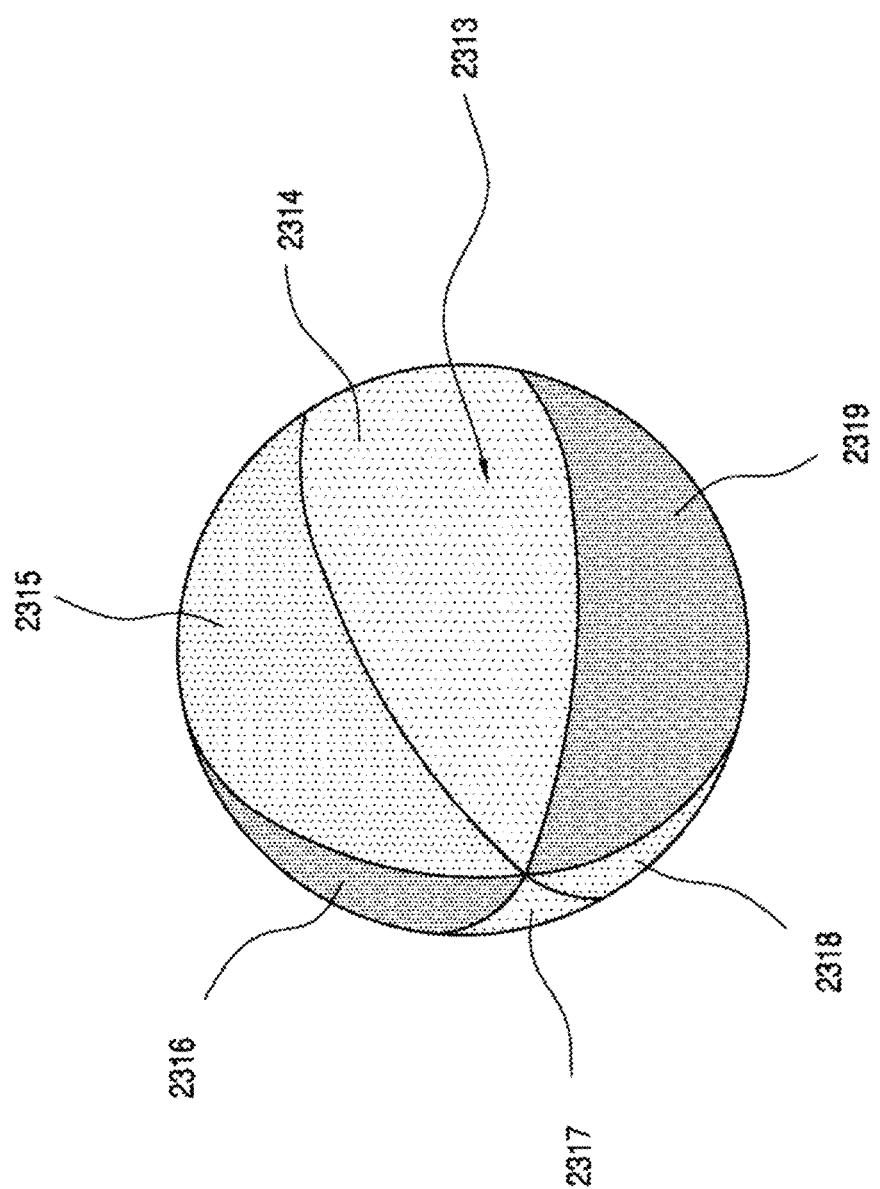
FIG. 23 illustrates an electronic device, according to an embodiment.

Referring again to FIG. 15, in some embodiments, method 1500 can comprise activity 1507 of arranging a first electronic device element (e.g., a first electronic device tile) adjacent to one or more other electronic device elements (e.g., one or more other electronic device tiles), such as, for example, in an array grid. In some embodiments, the first electronic device element (e.g., a first electronic device tile) can be arranged adjacent to the other electronic device element(s) (e.g., the other electronic device tile(s)) in a three-dimensional arrangement, such as, for example, as shown for electronic device 2300 (FIG. 23). Although any suitable three-dimensional arrangement can be implemented, exemplary three-dimensional arrangements can comprise a sphere, a cube, etc.

The first electronic device element can comprise the device substrate, active section(s), and wavy metal interconnect(s) described above with respect to activities 1501-1503. Each of the other electronic device element(s) can be similar or identical to the first electronic device element. Further, the edge portion width dimension of the first electronic device element can be approximately equal to at least one or all edge portion width dimensions of the other electronic device element(s). Meanwhile, performing activity 1507 can comprise arranging the device substrate of the first electronic device element adjacent to one or more other device substrates of the other electronic device element(s). In some embodiments, the electronic device of method 1500 can comprise the first electronic device element and any other electronic device element(s) that are applicable.

In these embodiments, each of the other electronic device element(s) can be provided (e.g., manufactured) by performing activities 1501-1504 again for at least one or all other electronic device elements of the other electronic device element(s). Further still, in some embodiments, activity 1505 and/or activity 1506 also can be performed for at least one or all other electronic device elements of the other electronic device element(s). However, in further embodiments, activity 1505 can be performed with respect to the first electronic device element and at least one or all other electronic device elements of the other electronic device element(s) as a single activity rather than as separate activities for each of the first electronic device element and the other electronic device element(s), respectively. For example, in some embodiments, the at least one or all other electronic device elements of the other electronic device element(s) can be supported by the same support structure as the first electronic device element. Likewise, in some embodiments, activity 1506 may be performed for some or all of the first electronic device element and the other electronic device element(s). Meanwhile, in other embodiments, activity 1505 and/or activity 1506 can be omitted with respect to at least one or all of the other electronic device element(s). Further, activity 1507 can be performed after activities 1501, 1502, 1503, after or approximately simultaneously with activity 1504, after or approximately simultaneously with activity 1505 when applicable, and after 1506 when applicable, for the first electronic device element and the other electronic device element(s). In some embodiments, when applicable, activity 1507 can be performed as separate activities with respect to the first electronic device element and two or more electronic device elements of the other electronic device element(s). Meanwhile, in other embodiments, activity 1507 can be omitted, such as, for example, when the electronic device of method 1500 is implemented with only the first electronic device element.

The array grid can comprise an array grid sheet length and an array grid sheet width. The array grid sheet length can be defined in terms of a number of electronic device elements of which the electronic device of method 1500 comprises in a longitudinal direction, and the array grid sheet width can be defined in terms of a number of electronic device elements of which the electronic device of method 1500 comprises in a lateral direction when the first electronic device element and the other electronic device element(s) are arranged in the array grid. In many embodiments, the array grid can comprise a regular Cartesian grid, but in other embodiments, can comprise any other suitable type of grid. For instance, in these other examples, the array grid can be asymmetric and/or discontinuous.

In many embodiments, activity 1902 (FIG. 19) can be performed with respect to the first electronic device element and/or at least one or all other electronic device elements of the other electronic device element(s) to achieve a desired arrangement of the first electronic device element and the other electronic device element(s) upon performing activity 1507. That is, the arrangement provided by activity 1507 can determine a shape of the electronic device of method 1500 upon completion of method 1500.

Meanwhile, in further embodiments, a seam (e.g., gap) between any two electronic device elements of the electronic device of method 1500 when the first electronic device element and at least one or all other electronic device elements of the other electronic device element(s) are adjacently arranged can comprise a seam distance. The seam distance can refer to a distance between the device portions of the two electronic device elements. A value of the seam distance can comprise a value of approximately 0 micrometers where no perimeter portions of the device substrates of the two electronic device elements are folded between the two electronic device elements, a value equal to approximately one edge portion thickness dimension of one electronic device element of the two electronic device elements where one perimeter portion of the device substrates of the two electronic device elements is folded between the two electronic device elements, and a value equal to approximately both edge portion thickness dimensions of the two electronic device elements where a perimeter portion of both device substrates of the two electronic device elements are folded between the two electronic device elements. For example, the seam distance can be greater than or equal to approximately 0 micrometers and less than or equal to approximately 40 micrometers.

Further, method 1500 can comprise activity 1508 of mechanically coupling (e.g., bonding, sewing, etc.) the first electronic device element to itself and/or at least one or all other electronic device elements of the other electronic device element(s). In these embodiments, when activity 1505 comprises activity 1703 (FIG. 17), performing activity 1508 can comprise coupling the first electronic device element to itself and/or at least one or all other electronic device elements of the other electronic device element(s) such that the first electronic device, and if applicable, the at least one or all other electronic device elements of the other electronic device element(s) form a closed volume. In these embodiments, performing activity 1703 (FIG. 17) can comprise filling the closed volume with the fluid(s) of activity 1703.

In some embodiments, activity 1508 can be performed as part of activity 1507. In further embodiments, when applicable, activity 1508 can be performed as separate activities with respect to the first electronic device element and two or more electronic device elements of the other electronic device element(s). Meanwhile, in other embodiments, activity 1508 can be omitted, such as, for example, when the electronic device of method 1500 is implemented with only the first electronic device element.

Meanwhile, method 1500 can comprise activity 1509 of electrically coupling at least one wavy metal interconnect of the wavy metal interconnect(s) of the first electronic device element to at least one wavy metal interconnect of the wavy metal interconnect(s) of the other electronic device element(s). In particular, performing activity 1509 can comprise electrically coupling together the wavy metal interconnect(s) of the first electronic device element and the other electronic device element(s) so that the wavy metal interconnect(s) are electrically continuous across the electronic device of method 1500. The advantages of performing activity 1509 are discussed further below.

In some embodiments, activity 1509 can be performed as part of activity 1507 and/or 1508. In further embodiments, when applicable, activity 1509 can be performed as separate activities with respect to the first electronic device element and two or more electronic device elements of the other electronic device element(s). Meanwhile, in other embodiments, activity 1509 can be omitted, such as, for example, when the electronic device of method 1500 is implemented with only the first electronic device element.

In these or other embodiments, row and column driver circuitry can be electrically coupled to one or more data line(s) (e.g., the wavy metal interconnect(s)) of the electronic device to operate (e.g., read out) the electronic device. Generally, activity 1509 can be performed when it is desirable to implement the electronic device of method 1500 with row and column driver circuitry operating the electronic device of method 1500 as a whole. Alternatively, activity 1509 can be omitted when the electronic device comprises the first the first electronic device element and the other electronic device element(s) and it is desirable to implement the electronic device of method 1500 with row and column driver circuitry operating the first electronic device element and the other electronic device element(s) independently, as discussed further below.

For example, it may be desirable to implement the electronic device of method 1500 with row and column driver circuitry operating the electronic device of method 1500 as a whole to reduce manufacturing costs of the electronic device by reducing a quantity of row and column driver circuitry, amplifiers, etc. necessary to operate the electronic device of method 1500. Further, it may be desirable to implement the electronic device of method 1500 with row and column driver circuitry operating the electronic device of method 1500 as a whole to sequester sources of heat (e.g., the row and column driver circuitry, amplifiers, etc.) to a periphery of the electronic device of method 1500. In particular, it may be advantageous to sequester sources of heat to the periphery of the electronic device of method 1500 when the electronic device comprises an active matrix array of a medical imaging system. For example, in some embodiments, sequestering sources of heat to the periphery of the electronic device of method 1500 may prevent a patient from being burned by the sources of heat when the medical imaging system is being operated to image the patient.

Alternatively, activity 1509 can be omitted, and the first electronic device element and the other electronic device element(s) can be operated independently, when it is desirable to improve manufacturing and/or operational yield of the electronic device of method 1500 and/or to reduce electric noise generated when operating the electronic device of method 1500. Notably, improving manufacturing yield can reduce manufacturing costs, and reducing electric noise can improve sensitivity (e.g., accuracy) of detecting semiconductor electronic device(s) integrated in the electronic device of method 1500.

For example, in many embodiments, as a quantity of semiconductor devices integrated in a unitary electronic device increases, the likelihood that one or more of the semiconductor devices will be defective can also increase, such as, for example, as a result of line out or pixel out manufacturing defects. Thus, because the electronic device of method 1500 can comprise the first electronic device element, and optionally, the other electronic device element(s), defective electronic device element(s) can be replaced without sacrificing the entirety of the electronic device. That is, because the first electronic device element and the other electronic device element(s) can be similar or identical to each other, the first electronic device element and the other electronic device element(s) can be fungible, and swapped out as desirable or needed. Not only can this permit manufacturing yield increases when defective electronic device element(s) are swapped out during manufacturing, but in some embodiments, operational yield can also be increased because damaged electronic device element(s) can be replaced as well.

Meanwhile, in many embodiments, implementing the electronic device of method 1500 so that the first electronic device element and the other electronic device element(s) are operable independently of each other can reduce electric noise generated when operating the electronic device of method 1500 by partitioning the data line(s) of the electronic device discretely among the first electronic device element and the other electronic device element(s). Specifically, partitioning data line(s) of the electronic device discretely among the first electronic device element and the other electronic device element(s) and operating each of the first the first electronic device element and the other electronic device element(s) with separate row and column device drivers, and optionally with separate related components (e.g., amplifiers, etc.) can reduce length(s) of the data line(s), which in turn can reduce electric noise generated by operating the data line(s).

Notably, as data line length increases in an electronic device such as the electronic device of method 1500, electric noise generated by the data line can increasingly dominate a total electric noise of the electronic device. Accordingly, minimizing the length of a data line can minimize a contribution of electric noise of the data line to the total electric noise of the electronic device. Said generally, the electric noise of the data line ($\sigma_D$) results from resistive Johnson-thermal electric noise in combination with electric noise associated with the capacitance of the data line. More specifically, the contribution of electric noise by a data line ($\sigma_D$) can be calculated in electrons (e−) at an input of a charge amplifier of the data line using Equation (1) as follows:

$$\sigma_D = \frac{\left[\sqrt{4KTR\Delta f} \times C\right]}{q}, \qquad (1)$$

where $\Delta f$ represents bandwidth, K represents Boltzmans constant of $1.381 \times 10^{-23}$ Joules per degree Kelvin, T represents temperature in degrees Kelvin, R represents a resistance of the data line, and C represents a capacitance of the data line. Referring to Equation (1), it can be seen that the electric noise of the data line (c) is a direct function of the resistance of the data line (R) and the capacitance of the data line (C). Reducing the length of the data line reduces both the resistance and capacitance of the data line and thereby reduces the electric noise of the data line. Meanwhile, the sensitivity (e.g., accuracy) of a detecting semiconductor electronic device can be directly proportional to a signal to noise ratio at an input of a charge amplifier of a data line coupled to the detecting semiconductor electronic device, with lower electric noise translating into higher sensitivity (e.g., accuracy).

Now, as introduced above, the zero edge of the electronic device of method 1500 can provide many advantages. In particular, performing activity 1504 permits row and driver circuitry and other related structures to be set off from the device portion(s) of the device substrate(s) of the electronic device of method 1500. As a result, the electronic device of method 1500 can comprise multiple electronic device element(s), as discussed above, while effectively having a continuous edge to edge active area (e.g., display or imaging area) of the electronic device.

In many embodiments, the electronic device of method 1500 can overcome the disadvantages of conventional medical imaging devices regarding non-emitting/detecting regions, as introduced above, when the electronic device of method 1500 is implemented as a medical imaging device because objects and patients can be imaged nearly out to the furthest edges of the electronic device of method 1500. Meanwhile, seams between multiple electronic device element(s) arranged in combination can be effectively eliminated because the edge portion width dimension(s) of the perimeter portion(s) of the device substrate(s) can be so small. For example, the emitter pixels of a typical high definition television display may comprise smallest cross dimensions ranging between approximately 500 to 1000 micrometers and the detector pixels of a typical medical imaging (e.g., x-ray) device may comprise smallest cross dimensions of approximately 200 micrometers. As indicated above, seams between the multiple electronic device elements may range from greater than or equal to approximately 0 micrometers to less than or equal to approximately 40 micrometers, which by contract, renders the seams effectively optically invisible to a human eye.

Figure 22:
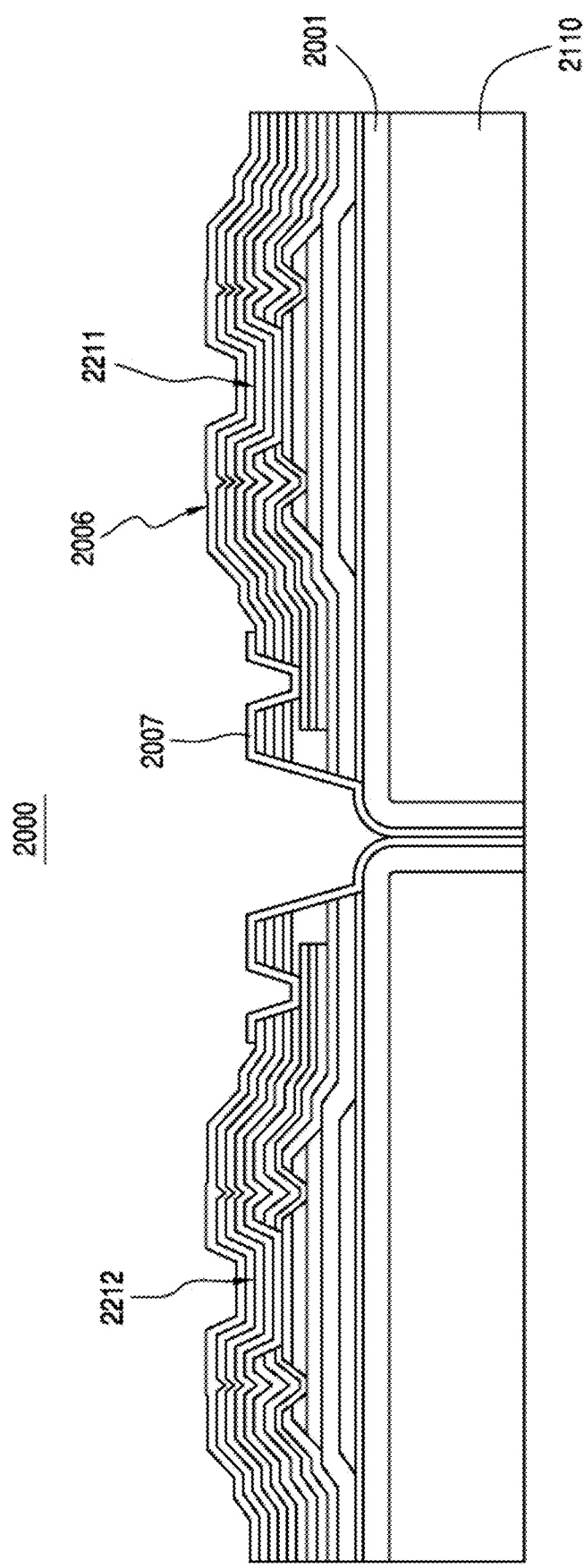
FIG. 22 illustrates another partial cross-sectional view of the electronic device, according to the embodiment of FIG. 20.

Turning ahead in the drawings, FIG. 22 illustrates another partial cross-sectional view of electronic device 2000, according to the embodiment of FIG. 20. In these embodiments, electronic device 2000 can be similar or identical to the electronic device of method 1500 (FIG. 15), such as, for example, after arranging a first electronic device element (e.g., a first electronic device tile) adjacent to one or more other electronic device elements (e.g., one or more other electronic device tiles), according to the method of FIG. 15. Accordingly, electronic device 2000 can comprise first electronic device element 2211 and second electronic device element 2212. In many embodiments, first electronic device element 2211 can be similar or identical to the first electronic device element described above with respect to method 1500 (FIG. 15), and second electronic device element 2212 can be similar or identical to one of the other electronic device element(s) described above with respect to method 1500 (FIG. 15). Further, first electronic device element 2211 can comprise device substrate 2001, active section 2006, wavy metal interconnect 2007, and support structure 2110.

Meanwhile, turning to the next drawing, FIG. 23 illustrates electronic device 2300, according to an embodiment. Electronic device 2300 can be similar or identical to the electronic device described above with respect to method 1500 (FIG. 15) and/or to electronic device 2000 (FIGS. 20-22). Accordingly, electronic device 2300 can comprise multiple electronic device elements 2313 comprising first electronic device element 2314, second electronic device element 2315, third electronic device element 2316, fourth electronic device element 2317, fifth electronic device element 2318, and sixth electronic device element 2319. In some embodiments, electronic device 2300 can be supported by a support structure or by one or more fluids, as described above with respect to method 1500 (FIG. 15). Further, each of multiple electronic device elements 2313 can be similar or identical to one of the first electronic device element and the other electronic device element(s) described above with respect to method 1500 (FIG. 15).

Figure 24:
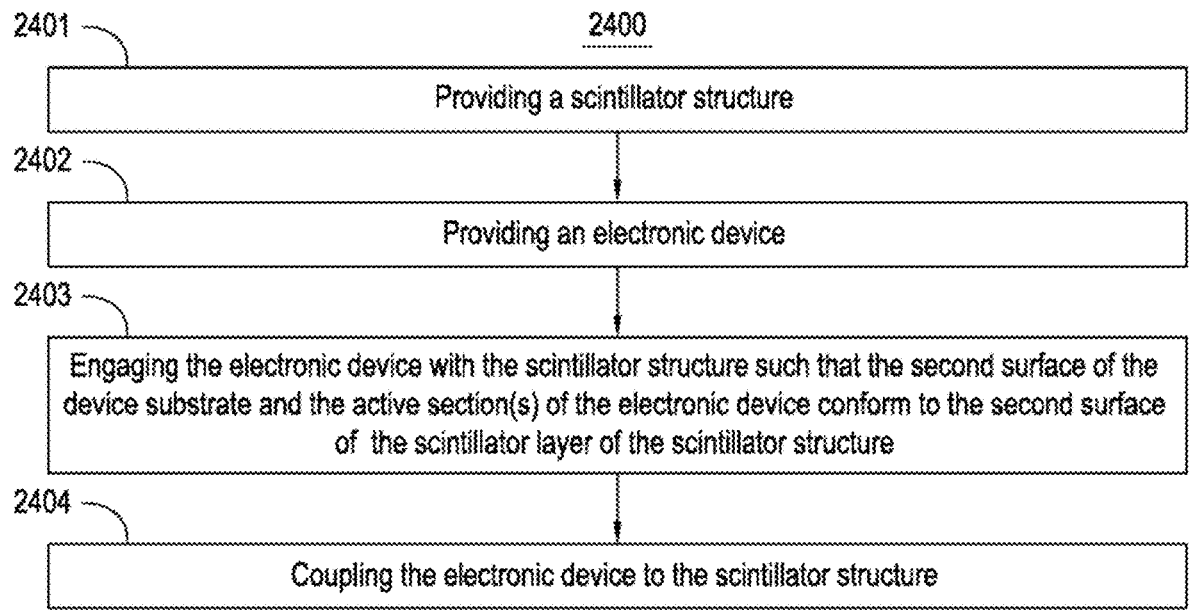
FIG. 24 illustrates an example of a method, according to an embodiment.

Turning ahead in the drawings, FIG. 24 illustrates an example of a method 2400, according to an embodiment. Method 2400 is merely exemplary and is not limited to the embodiments presented herein. Method 2400 can be employed in many different embodiments or examples not specifically depicted or described herein. In some embodiments, the activities of method 2400 can be performed in the order presented. In other embodiments, the activities of method 2400 can be performed in any other suitable order. In still other embodiments, one or more of the activities in method 2400 can be combined or skipped.

In many embodiments method 2400 can comprise a method of providing (e.g., manufacturing) an imaging system. The imaging system can be operable to image (e.g., digitally image) one or more objects (e.g., one or more persons, one or more body parts and/or organs of the person(s), one or more vehicle hulls, one or more vessels, one or more articles of luggage, etc.). Exemplary vessel(s) can comprise one or more pipes, one or more boilers, one or more valves, one or more ducts, etc. In some embodiments, the imaging system can be operable for medical, industrial, and/or security imaging. Further, the imaging system can be operable with a variety of imaging techniques (e.g., radiography, fluoroscopy, tomography, etc.).

In further embodiments, the imaging system can comprise a 3D conformal imaging system. For example, in these or other embodiments, the imaging system can conform and/or can be conformed to the object(s) (e.g., 3D objects) to be imaged by the imaging system. Consequently, in some embodiments, the imaging system can provide better quality imaging of the object(s) than conventional imaging systems may permit and/or can be manipulated to occupy spaces in which conventional imaging systems may not fit.

Figure 25:
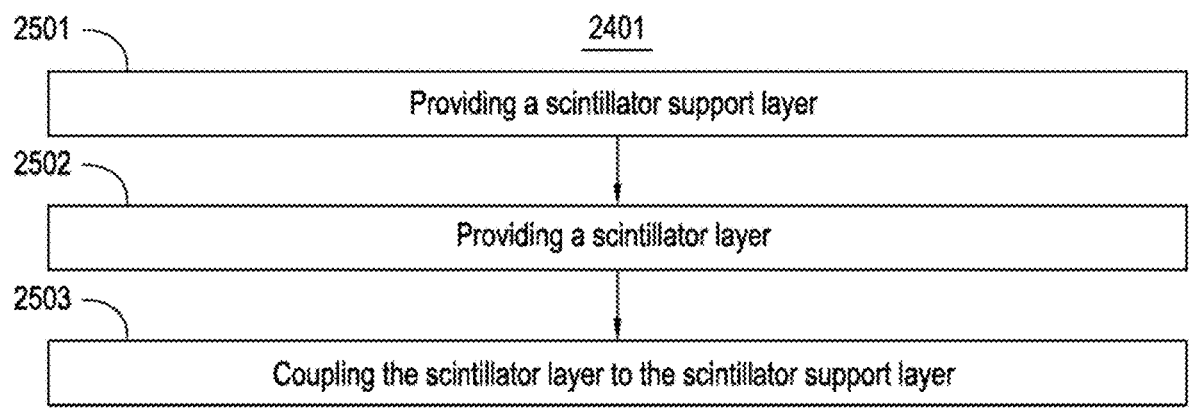
FIG. 25 illustrates an exemplary activity of providing a scintillator structure, according to the embodiment of FIG. 24.

In many embodiments, method 2400 can comprise activity 2401 of providing a scintillator structure. The scintillator structure can be operable as a scintillator of the imaging system. FIG. 25 illustrates an exemplary activity 2401, according to the embodiment of FIG. 24.

For example, in many embodiments, activity 2401 can comprise activity 2501 of providing a scintillator support layer. The scintillator support layer can comprise a first side and a second side opposite the first side. Further, the scintillator support layer can comprise a first surface and a second surface opposite the first surface. In these embodiments, the first surface of the scintillator support layer can be located at the first side of the scintillator support layer, and the second surface of the scintillator support layer can be located at the second side of the scintillator support layer.

In these or other embodiments, the second surface of the scintillator support layer can comprise a substantially non-planar surface. In many embodiments, a substantially non-planar surface can refer to any surface occupying three dimensions. For example, a substantially non-planar surface can refer to a surface devoid of any planar surfaces (e.g., a curved surface) or a manifold (e.g., a topological space comprising multiple points and resembling Euclidean space proximal to each of the multiple points) that is non-planar. Further, a non-planar manifold can refer to a continuous surface comprising multiple sub-surfaces with at least two sub-surfaces of the multiple sub-surfaces being non-planar with each other. In many embodiments, as the number of sub-surfaces increases and/or as the area or areas of the sub-surfaces decrease, the manifold can increasingly approximate a surface devoid of any planar surfaces (e.g., a curved surface). Exemplary substantially non-planar surfaces can comprise an ellipsoid, a spheroid (e.g., sphere), a paraboloid (e.g., elliptic paraboloid, circular paraboloid, hyperbolic paraboloid), certain hyperboloids, an elliptic cone, a circular cone, an elliptic cylinder, a circular cylinder, a parabolic cylinder, or a prism (e.g., cube).

In many embodiments, the scintillator support layer can be operable to structurally support and/or protect the scintillator layer described below with respect to activity 2502. In these or other embodiments, the scintillator support layer comprises one or more scintillator support layer materials. The scintillator support layer material(s) can comprise one or more materials configured to structurally support and/or protect the scintillator layer. Accordingly, the scintillator support layer material(s) can comprise one or more polymer, one or more metal, and/or one or more ceramic materials. The scintillator support layer material(s) implemented for the scintillator support layer can be selected according to a manner by which the substantially non-planar surface is formed, and vice versa. Meanwhile, the scintillator support layer material(s) implemented for the scintillator support layer can be selected according to one or more material properties (e.g., strength, density, etc.) of the scintillator support layer material(s). For example, the strength(s) of the scintillator support layer material(s) can impact an ability of the scintillator support layer to support the scintillator layer, and the density or densities of the scintillator support layer material(s) can impact an ability of the scintillator support layer to pass ionizing radiation. In some embodiments, the scintillator support layer material(s) can comprise one or more thermoplastic polymers.

In many embodiments, the scintillator support layer comprises a scintillator support layer thickness. The scintillator support layer thickness can refer to a dimension of the scintillator support layer extending between the first and second surfaces of the scintillator support layer. In many embodiments, the scintillator support layer thickness can be approximately constant. The scintillator support layer thickness can comprise any suitable thickness. However, in many embodiments, the scintillator support layer thickness can be implemented to be as small (e.g., thin) as possible while still providing sufficient structural support to the scintillator layer described below with respect to activity 2502. For example, in many embodiments, the scintillator support layer thickness can be greater than or equal to approximately 200 micrometers and less than or equal to approximately 300 micrometers. Further, in some embodiments, the scintillator support layer thickness can be approximately 250 micrometers.

Figure 26:
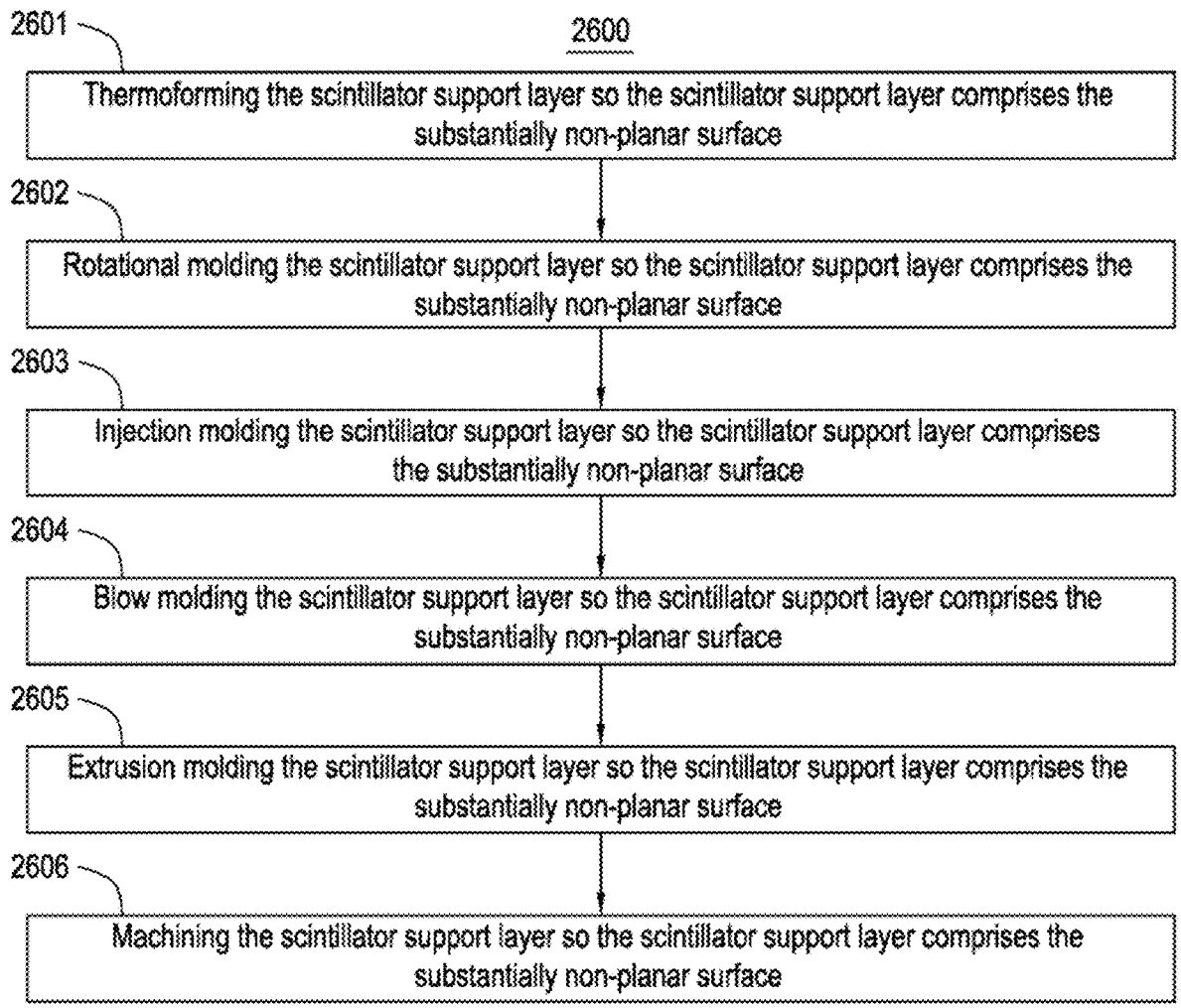
FIG. 26 illustrates an exemplary activity of forming a scintillator support layer of the scintillator structure so the scintillator support layer comprises a substantially non-planar surface, according to the embodiment of FIG. 24.

In many embodiments, performing activity 2501 can comprise forming the scintillator support layer so the scintillator support layer comprises the substantially non-planar surface. In these embodiments, forming the scintillator support layer so the scintillator support layer comprises the substantially non-planar surface can be performed using any suitable manufacturing technique or techniques. FIG. 26 illustrates an exemplary activity 2600 of forming the scintillator support layer so the scintillator support layer comprises the substantially non-planar surface, according to the embodiment of FIG. 24.

For example, activity 2600 can comprise at least one of: (i) activity 2601 of thermoforming the scintillator support layer so the scintillator support layer comprises the substantially non-planar surface; (ii) activity 2602 of rotational molding the scintillator support layer so the scintillator support layer comprises the substantially non-planar surface; (iii) activity 2603 of injection molding the scintillator support layer so the scintillator support layer comprises the substantially non-planar surface; (iv) activity 2604 of blow molding the scintillator support layer so the scintillator support layer comprises the substantially non-planar surface; (v) e activity 2605 of extrusion molding the scintillator support layer so the scintillator support layer comprises the substantially non-planar surface; or (vi) activity 2606 of machining the scintillator support layer so the scintillator support layer comprises the substantially non-planar surface. As noted previously, the scintillator support layer material(s) implemented for the scintillator support layer can be selected according to a manner by which the substantially non-planar surface is formed, and vice versa. For example, in many embodiments, when activity 2601 is performed, the scintillator support layer material(s) can comprise at least one thermoplastic polymer, and the scintillator support layer can be heated to a pliable forming temperature and molded in a mold so the scintillator support layer comprises the substantially non-planar surface.

In some embodiments, activity 2600 or one or more of activities 2601-2606 can be omitted. In these embodiments, the scintillator support layer can be pre-fabricated to comprise the substantially non-planar surface.

In further embodiments, the first surface of the scintillator support layer can comprise a test surface of the scintillator support layer. In these embodiments, the test surface can be operable to be proximal to and/or contact the object(s) to be imaged by the imaging system. Accordingly, in many embodiments, the test surface can complement or approximately complement the contour of the substantially non-planar surface of the scintillator support layer, and/or a surface of the object(s) being imaged by the imaging system. As a result, as discussed in greater detail below, the test surface can conform or approximately conform to the surface of the object(s) being imaged by the imaging system.

Referring now back to FIG. 24, in many embodiments, activity 2401 can comprise activity 2502 of providing a scintillator layer. The scintillator layer can comprise a first side and a second side opposite the first side. Further, the scintillator layer can comprise a first surface and a second surface opposite the first surface. In these embodiments, the first surface of the scintillator layer can be located at the first side of the scintillator layer, and the second surface of the scintillator support layer can be located at the second side of the scintillator layer.

Further, the scintillator layer can be configured to scintillate. That is, the scintillator layer can be configured to luminesce when exposed to ionizing radiation. Accordingly, the scintillator layer can comprise one or more scintillator layer materials. The scintillator layer material(s) can comprise one or more phosphor materials, and in some embodiments, can comprise one or more binder materials configured to bind the phosphor material(s) together.

For example, when the phosphor material(s) are implemented as grains, the grains can be suspended in the binder material(s) and bound together by the binder material(s). In some embodiments, the grains can comprise a largest dimension (e.g., diameter) of greater than or equal to approximately 2 micrometers and less than or equal to approximately 30 micrometers.

Exemplary phosphor material(s) can comprise at least one of barium fluoride ($BaF_2$), europium doped calcium fluoride ($CaF_2$:Eu), bismuth germinate ($Bi_4Ge_3O_{12}$), cadmium tungstate ($CdWO_4$), thallium doped cesium iodide (CsI:Tl), sodium doped cesium iodide (CsI:Na), cesium iodide, terbium doped gadolimium oxysulfide ($Gd_2O_2S$:Tb), cerium doped lanthanum bromide ($LaBr_3$:Ce), cerium doped lanthanum chloride ($LaCl_2$:Ce), lead tungstate ($PbWO_4$), lutetium iodide ($LuI_3$), lutetium oxyorthosilicate ($Lu_2SiO_5$), lutetium oxyorthosilicate ($Lu_2SiO_5$), cesium doped lutetium-yttrium oxyorthosilicate ($Lu_{1.8}Y_{0.2}SiO_5$:Ce), thallium doped sodium iodide (NaI:Tl), cesium doped yttrium aluminum garnet ($Y_3Al_5O_{12}$:Ce), silver doped zinc sulfide (ZnS:Ag), or zinc tungstate ($ZnWO_4$). Terbium doped gadolimium oxysulfide ($Gd_2O_2S$:Tb) can sometimes be referred to as Gadox. Meanwhile, exemplary binder(s) can comprise one or more adhesive materials (e.g., one or more acrylic adhesive materials, one or more epoxy materials, etc.).

In many embodiments, the scintillator support layer comprises a scintillator layer thickness. The scintillator layer thickness can refer to a dimension of the scintillator support layer extending between the first and second surfaces of the scintillator layer. In many embodiments, the scintillator layer thickness can be approximately constant. The scintillator layer thickness can comprise any suitable thickness. However, in many embodiments, the scintillator support layer thickness can be implemented to be as small (e.g., thin) as possible while still being sufficiently luminescent for the operability of the scintillator structure. For example, in many embodiments, the scintillator layer thickness can be greater than or equal to approximately 50 micrometers and less than or equal to approximately 150 micrometers. Further, in some embodiments, the scintillator layer thickness can be approximately 100 micrometers.

Figure 27:
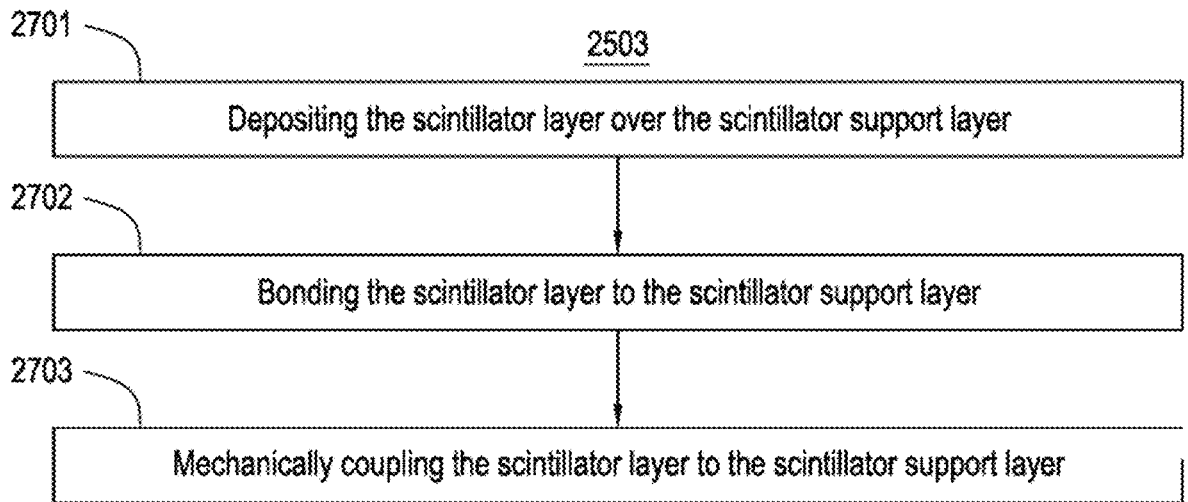
FIG. 27 illustrates an exemplary activity of coupling a scintillator layer of the scintillator structure to the scintillator support layer, according to the embodiment of FIG. 24.

In many embodiments, activity 2401 can comprise activity 2503 of coupling the scintillator layer to the scintillator support layer. In these or other embodiments, the first surface of the scintillator layer can be coupled to the substantially non-planar surface of the scintillator support layer such that the second surface of the scintillator layer comprises a same or similar contour of the substantially non-planar surface of the scintillator support layer. That is, the second surface of the scintillator layer can take on the same contour or a similar contour to that of the substantially non-planar surface of the scintillator support layer as a result of the first surface of the scintillator layer being coupled to the substantially non-planar surface of the scintillator support layer. FIG. 27 illustrates an exemplary activity 2503, according to the embodiment of FIG. 24.

For example, in many embodiments, activity 2503 can comprise activity 2701 of depositing the scintillator layer over the scintillator support layer. In these embodiments, activity 2701 can be performed using any suitable deposition technique or techniques (e.g., chemical vapor deposition, such as, for example plasma-enhanced chemical vapor deposition, sputtering, molecular beam epitaxy, spin-coating, spray-coating, extrusion coating, preform lamination, slot die coating, screen lamination, sedimentation, and/or screen printing, etc.).

In other embodiments, activity 2503 can comprise activity 2702 of bonding the scintillator layer to the scintillator support layer. In these embodiments, any suitable adhesive material or materials can be implemented to bond the scintillator layer to the scintillator support layer. Exemplary bonding material(s) can comprise acrylic adhesive, epoxy, etc. In many embodiments, the adhesive material(s) can bond the scintillator layer to the scintillator support layer directly, and in other embodiments, the adhesive material(s) can bond the scintillator layer to the scintillator support layer indirectly, such as, for example, as part of an adhesive tape.

In still other embodiments, activity 2503 can comprise activity 2703 of mechanically coupling the scintillator layer to the scintillator support layer, such as, for example, using one or more coupling mechanisms (e.g., fasteners). In these embodiments, any suitable coupling mechanism(s) can be implemented.

In some embodiments, when one of activities 2701-2703 are performed, the other two of activities 2701-2703 can be omitted. However, in other embodiments, at least two of activities 2701-2703 can be performed.

Referring now back to FIG. 25, in some embodiments, when performing activity 2501 comprises forming the scintillator support layer so the scintillator support layer comprises the substantially non-planar surface, activity 2503 can be performed before forming the scintillator support layer so the scintillator support layer comprises the substantially non-planar surface. In these embodiments, forming the scintillator support layer so the scintillator support layer comprises the substantially non-planar surface can occur while the scintillator layer is coupled to the scintillator support layer.

In other embodiments, when performing activity 2501 comprises forming the scintillator support layer so the scintillator support layer comprises the substantially non-planar surface, activity 2503 can be performed after forming the scintillator support layer so the scintillator support layer comprises the substantially non-planar surface. In these embodiments, performing activity 2503 can comprise coupling the first surface of the scintillator layer to the substantially non-planar surface of the scintillator support layer. Further, in these embodiments, when activity 2701 is performed, performing activity 2701 using certain deposition techniques (e.g., spray-coating) may provide superior results to using other deposition techniques (e.g., sedimentation, screen printing, etc.) due to the substantially non-planar surface of the scintillator support layer.

Referring now back to FIG. 24, in further embodiments, method 2400 can comprise activity 2402 of providing an electronic device. Although the electronic device can comprise any deformable electronic device configured to engage the scintillator structure as described below, in many embodiments, the electronic device can comprise a deformable electronic device. For example, in various embodiments, the electronic device can be flexible and/or stretchable. In these or other embodiments, the electronic device can be similar or identical to the electronic device described above with respect to method 100 (FIG. 1) and/or with respect to method 1500 (FIG. 15). Further, the electronic device can be similar or identical to electronic device 300 (FIGS. 3, 6, 7, & 9), electronic device 2000 (FIGS. 20-22), and/or electronic device 2300 (FIG. 23). In still further embodiments, the electronic device can be operable as an active matrix array of the imaging system (e.g., 3D conformal imaging system).

The electronic device can comprise a device substrate and one or more active sections. In many embodiments, the device substrate can be similar or identical to the device substrate described above with respect to method 100 (FIG. 1) and/or method 1500 (FIG. 15), to device substrate 304 (FIG. 3), to device substrate 1004 (FIG. 10), to device substrate 1104 (FIG. 11), to device substrate 1204 (FIG. 12), and/or to device substrate 2001 (FIG. 20); and/or the active section(s) can be similar or identical to the active section(s) described above with respect to method 100 (FIG. 1) and/or method 1500 (FIG. 15), to active section 1023 (FIG. 10), to active section 1123 (FIG. 11), to active section 1223 (FIG. 12), to active section 1323 (FIG. 13), and/or to active section 2006 (FIG. 20).

Accordingly, the device substrate can comprise a first side and a second side opposite the first side. Further, the device substrate can comprise a first surface and a second surface opposite the first surface. In these embodiments, the first surface of the device substrate can be located at the first side of the device substrate, and the second surface of the device substrate can be located at the second side of the device substrate. Meanwhile, the active section(s) can be located over the second surface of the device substrate, and in many embodiments, can comprise one or more detector pixels configured to detect photons emitted by the scintillator structure as a result of the scintillator structure receiving ionizing radiation at the scintillator layer.

Meanwhile, in many embodiments, method 2400 can comprise activity 2403 of engaging the electronic device with the scintillator structure such that the second surface of the device substrate and the active section(s) of the electronic device conform to the second surface of the scintillator layer of the scintillator structure. In many embodiments, when the electronic device engages with the scintillator structure, the active section(s) of the electronic device can be positioned proximal to the scintillator layer of the scintillator structure, and in further embodiments, can directly contact the scintillator layer of the scintillator structure.

Accordingly, in some embodiments, performing activity 2403 can comprise locating or bringing into contact the electronic device with the scintillator structure. In these or other embodiments, performing activity 2403 can comprise locating or bringing into contact the active section(s) of the electronic device with the scintillator layer of the scintillator structure. Further, in these or other embodiments, performing activity 2403 can comprise holding the electronic device in contact with the scintillator structure, such as, for example, with a force applicator. Although a force applicator can comprise any suitable mechanism configured to apply continuous force to the first surface of the device substrate so that the scintillator structure maintains engagement with the electronic device, an exemplary force applicator can comprise compressible foam that can be compressed and expand to apply continuous force to the first surface of the device substrate. In these embodiments, an opposing force can be applied to the first surface of the scintillator support layer by the object(s) being imaged.

Figure 28:
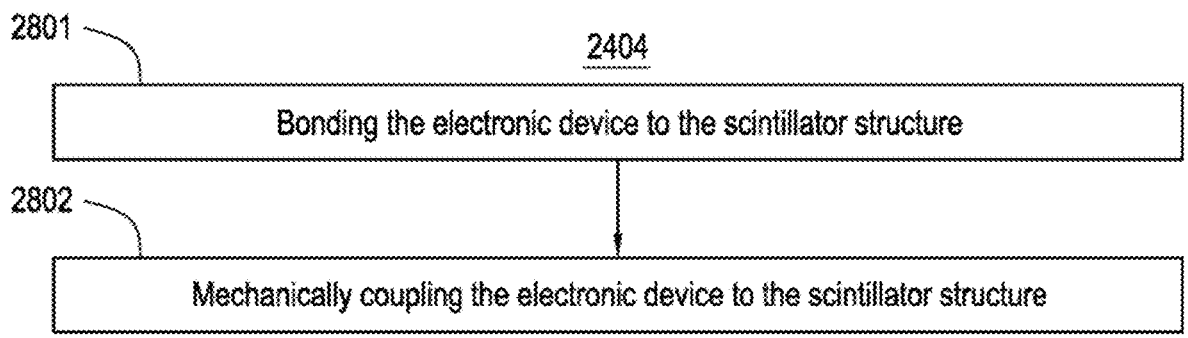
FIG. 28 illustrates an exemplary activity of coupling an electronic device to the scintillator structure, according to the embodiment of FIG. 24.

Further, in some embodiments, method 2400 can comprise activity 2404 of coupling the electronic device to the scintillator structure. In some embodiments, activity 2404 can be omitted. FIG. 28 illustrates an exemplary activity 2404, according to the embodiment of FIG. 24.

For example, in some embodiments, activity 2404 can comprise activity 2801 of bonding the electronic device to the scintillator structure. In these embodiments, any suitable adhesive material or materials can be implemented to bond the electronic device to the scintillator structure. Exemplary bonding material(s) can comprise acrylic adhesive, epoxy, etc. In many embodiments, the adhesive material(s) can bond the electronic device to the scintillator structure directly, and in other embodiments, the adhesive material(s) can bond the electronic device to the scintillator structure indirectly, such as, for example, as part of an adhesive tape.

In further embodiments, activity 2404 can comprise activity 2802 of mechanically coupling the electronic device to the scintillator structure, such as, for example, using one or more coupling mechanisms (e.g., fasteners). In these embodiments, any suitable coupling mechanism(s) can be implemented.

In some embodiments, when one of activities 2801 or 2802 is performed, the other one of activities 2801 and 2802 can be omitted. However, in other embodiments, activities 2801 and 2802 can both be performed.

When the electronic device is engaged with and/or coupled to the scintillator structure, the electronic device and scintillator structure can form an imaging structure of the imaging system. Because the test surface of the scintillator support layer of the scintillator structure can conform to the object(s) to be imaged by the imaging system, thus permitting the imaging structure as a whole to be brought closer to the object(s) during imaging, the imaging system can provide higher imaging resolution than would be possible with imaging systems with rigid and/or 2D active matrix arrays and scintillators. With higher imaging resolution, the imaging system can capture very small features in substantially non-planar surfaces of object(s) being imaged by the imaging system, such as, for example, hairline cracks in gas pipelines or in the corners of aircraft wings or submarine hulls. Meanwhile, because the electronic device (e.g., active matrix array) of the imaging system can be deformable, in some embodiments, the imaging system and/or imaging structure can be more robust than conventional imaging systems.

In many embodiments, but for the imaging structure, some or all of the remaining components of the imaging system can be implemented using conventional components (e.g., readout and drive electronics, amplifiers, computer systems, etc.). For example, in these or other embodiments, the imaging system can comprise any suitable electronic components configured to drive and readout an active matrix array of an imaging system and/or a computer system configured to interpret the data readout from the active matrix array and render the data in the form of a digital image. For purposes of brevity, further details concerning these conventional components are omitted, but (i) U.S. Non-Provisional patent application Ser. No. 14/642,550, filed Mar. 9, 2015, which published as United States Patent Application Publication No. 2016/0260765 on Sep. 8, 2016, and (ii) U.S. Non-Provisional patent application Ser. No. 14/642,563, filed Mar. 9, 2015, which published as United States Patent Application Publication No. 2016/0260768 on Sep. 8, 2016, each of which is incorporated by reference in its entirety, provide further discussion on such components.

Figure 29:
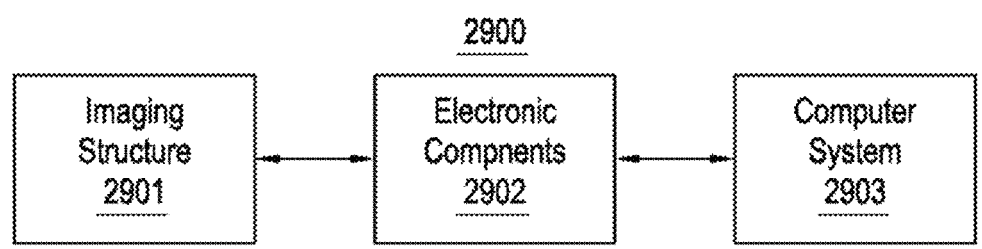
FIG. 29 illustrates a representative block diagram of an imaging system, according to an embodiment.

Skipping ahead now in the drawings, FIG. 29 illustrates a representative block diagram of an imaging system 2900, according to an embodiment. In many embodiments, imaging system 2900 can be similar or identical to the imaging system described above with respect to method 2400 (FIG. 24). Imaging system 2900 is merely exemplary and embodiments of the system are not limited to the embodiments presented herein. Imaging system 2900 can be employed in many different embodiments or examples not specifically depicted or described herein. In some embodiments, certain elements or modules of imaging system 2900 can perform various methods and/or activities of those methods. In these or other embodiments, the methods and/or the activities of the methods can be performed by other suitable elements or modules of imaging system 2900.

Figure 30:
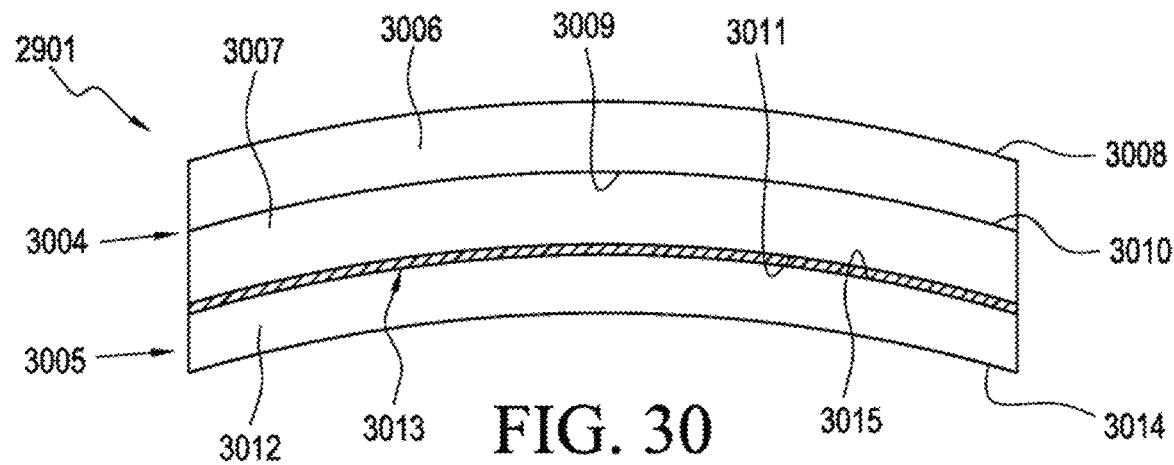
FIG. 30 illustrates an imaging structure of the imaging system, according to the embodiment of FIG. 29.

For example, in many embodiments, imaging system 2900 can comprise imaging structure 2901, electronic components 2902, and computer system 2903. In these or other embodiments, imaging structure 2901 can be similar or identical to the imaging structure described above with respect to method 2400 (FIG. 24); electronic components 2902 can be similar or identical to the electronic components described above with respect to method 2400 (FIG. 24); and/or computer system 2903 can be similar or identical to the computer system described above with respect to method 2400 (FIG. 24). FIG. 30 illustrates imaging structure 2901, according to the embodiment of FIG. 29.

Imaging structure 2901 can comprise scintillator structure 3004 and electronic device 3005. In many embodiments, scintillator structure 3004 can be engaged with and/or coupled to electronic device 3005. In some embodiments, scintillator structure 3004 can be similar or identical to the scintillator structure described above with respect to method 2400 (FIG. 24); and/or electronic device 3005 can be similar or identical to the electronic device described above with respect to method 2400 (FIG. 24).

In these or other embodiments, scintillator structure 3004 can comprise scintillator support layer 3006 and scintillator layer 3007. In many embodiments, scintillator support layer 3006 can be similar or identical to the scintillator support layer described above with respect to method 2400 (FIG. 24); and/or scintillator layer 3007 can be similar or identical to the scintillator layer described above with respect to method 2400 (FIG. 24).

Further, scintillator support layer 3006 can comprise first surface 3008 and second surface 3009, and scintillator layer 3007 can comprise first surface 3010 and second surface 3011. In many embodiments, first surface 3008 can be similar or identical to the first surface (e.g., test surface) of the scintillator support layer described above with respect to method 2400 (FIG. 24); second surface 3009 can be similar or identical to the second surface (e.g., substantially non-planar surface) of the scintillator support layer described above with respect to method 2400 (FIG. 24); first surface 3010 can be similar or identical to the first surface of the scintillator layer described above with respect to method 2400 (FIG. 24); and/or second surface 3011 can be similar or identical to the second surface of the scintillator layer described above with respect to method 2400 (FIG. 24).

Meanwhile, in these or other embodiments, electronic device 3005 can comprise device substrate 3012 and one or more active sections 3013. Device substrate 3012 can be similar or identical to the device substrate described above with respect to method 2400 (FIG. 24); and/or active section(s) 3013 can be similar or identical to the active section(s) described above with respect to method 2400 (FIG. 24).

Further, device substrate 3012 can comprise first surface 3014 and second surface 3015. In many embodiments, first surface 3014 can be similar or identical to the first surface of the device substrate described above with respect to method 2400 (FIG. 24); and/or second surface 315 can be similar or identical to the second surface of the device substrate described above with respect to method 2400 (FIG. 24).

Figure 31:
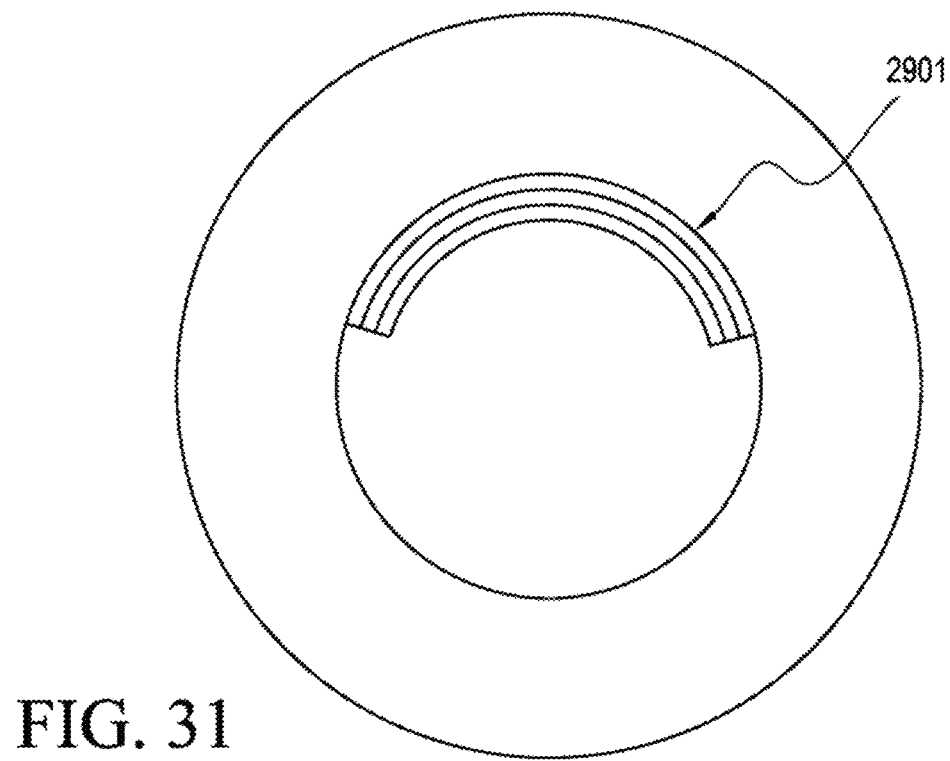
FIG. 31 illustrates the imaging structure disposed within the interior of a pipe, according to the embodiment of FIG. 29.

In many embodiments, first surface 3008 can be conformed to part or all of one or more objects (e.g., 3D objects) to be imaged by imaging system 2900. For example, the object(s) can include a pipe. FIG. 31 illustrates imaging structure 2901 disposed within the interior surface of a pipe, according to the embodiment of FIG. 29.

Figure 32:
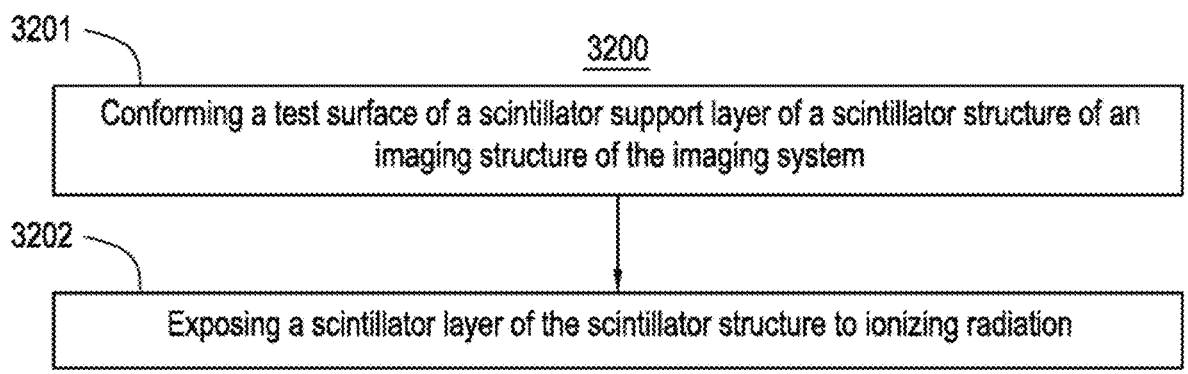
FIG. 32 illustrates an example of a method of using an imaging system, according to an embodiment.

Turning ahead in the drawings, FIG. 32 illustrates an example of a method 3200 of using an imaging system, according to an embodiment. The imaging system can be similar or identical to the imaging system described above with respect to method 2400 (FIG. 24) and/or to imaging system 2900 (FIG. 29). Method 3200 is merely exemplary and is not limited to the embodiments presented herein. Method 3200 can be employed in many different embodiments or examples not specifically depicted or described herein. In some embodiments, the activities of method 3200 can be performed in the order presented. In other embodiments, the activities of method 3200 can be performed in any other suitable order. In still other embodiments, one or more of the activities in method 3200 can be combined or skipped.

For example, method 3200 can comprise activity 3201 of conforming a test surface of a scintillator support layer of a scintillator structure of an imaging structure of the imaging system, such as for example, to one or more objects (e.g., 3D objects). The test surface can be similar or identical to the first surface (e.g., test surface) of the scintillator support layer described above with respect to method 2400 (FIG. 24) and/or to first surface 3008 (FIG. 30); the scintillator support layer can be similar or identical to the scintillator support layer described above with respect to method 2400 (FIG. 24) and/or to scintillator support layer 3006 (FIG. 30); the scintillator structure can be similar or identical to the scintillator structure described above with respect to method 2400 (FIG. 24) and/or to scintillator structure 3004 (FIG. 30); and/or the imaging structure can be similar or identical to the imaging structure described above with respect to method 2400 (FIG. 24) and/or to imaging structure 2901 (FIGS. 29-31).

Further, method 3200 can comprise activity 3202 of exposing a scintillator layer of the scintillator structure to ionizing radiation. In these embodiments, the scintillator layer can be similar or identical to the scintillator layer described above with respect to method 2400 (FIG. 24) and/or to scintillator layer 3007 (FIG. 30).

Although the invention has been described with reference to specific embodiments, it will be understood by those skilled in the art that various changes can be made without departing from the spirit or scope of the invention. Accordingly, the disclosure of embodiments is intended to be illustrative of the scope of the invention and is not intended to be limiting. It is intended that the scope of the invention shall be limited only to the extent required by the appended claims. To one of ordinary skill in the art, it will be readily apparent that the imaging systems and the methods of providing the imaging systems discussed herein may be implemented in a variety of embodiments, and that the foregoing discussion of certain of these embodiments does not necessarily represent a complete description of all possible embodiments. Rather, the detailed description of the drawings, and the drawings themselves, disclose at least one preferred embodiment, and may disclose alternative embodiments.

Generally, replacement of one or more claimed elements constitutes reconstruction and not repair. Additionally, benefits, other advantages, and solutions to problems have been described with regard to specific embodiments. The benefits, advantages, solutions to problems, and any element or elements that may cause any benefit, advantage, or solution to occur or become more pronounced, however, are not to be construed as critical, required, or essential features or elements of any or all of the claims.

Moreover, embodiments and limitations disclosed herein are not dedicated to the public under the doctrine of dedication if the embodiments and/or limitations: (1) are not expressly claimed in the claims; and (2) are or are potentially equivalents of express elements and/or limitations in the claims under the doctrine of equivalents.

What is claimed is:

1. An imaging system comprising:
   a scintillator structure; and
   an electronic device engaged with the scintillator structure, wherein:
   the scintillator structure comprises:
      a scintillator support layer; and
      a scintillator layer;
   the scintillator support layer comprises:
      a first substantially non-planar surface;
      a second substantially non-planar surface, the first substantially non-planar surface being approximately parallel to the second substantially non-planar surface; and
      a scintillator support layer thickness greater than approximately 200 micrometers and less than or equal to approximately 300 micrometers;
   the scintillator layer comprises:
      a first surface;
      a second surface opposite the first surface, the second surface being configured to scintillate; and
      one or more granular phosphor materials comprising a diameter of greater than or equal to approximately 2 micrometers and less than or equal to approximately 30 micrometers;
   the first surface of the scintillator layer is coupled to the second substantially non-planar surface of the scintillator support layer such that the second surface of the scintillator layer comprises a contour of the second substantially non-planar surface of the scintillator support layer;
   the electronic device comprises a device substrate and one or more active sections;
   the device substrate comprises a first surface and a second surface opposite the first surface of the device substrate;
   the one or more active sections are at the second surface of the device substrate; and
   the second surface of the device substrate and the one or more active sections conform to the second surface of the scintillator layer.

2. The imaging system of claim 1, wherein the device substrate comprises a device substrate thickness of less than or equal to approximately 25 micrometers.

3. The imaging system of claim 1, wherein the scintillator layer comprises one or more scintillator layer materials, and the one or more scintillator layer materials comprise terbium doped gadolinium oxysulfide.

4. The imaging system of claim 1, wherein the scintillator support layer comprises one or more scintillator support layer materials, and the one or more scintillator support layer materials comprise at least one thermoplastic polymer.

5. The imaging system of claim 1, wherein the scintillator layer comprises a scintillator layer thickness greater than or equal to approximately 50 micrometers and less than or equal to approximately 150 micrometers.

6. The imaging system of claim 1, wherein:
each respective active section of the one or more active sections comprises at least one respective semiconductor device; and
each respective semiconductor device of the at least one respective semiconductor device comprises at least one respective detector pixel.

7. The imaging system of claim 1, wherein the electronic device is coupled to the scintillator structure.

8. The imaging system of claim 1, wherein the first substantially non-planar surface and the second substantially non-planar surface comprise a non-planar manifold.

9. The imaging system of claim 1, wherein the scintillator layer is located over the scintillator support layer.

10. The imaging system of claim 1, wherein the device substrate further comprises a flexible substrate.

11. An imaging system comprising:
a scintillator structure; and
an electronic device engaged with the scintillator structure, wherein:
the scintillator structure comprises:
a scintillator support layer; and
a scintillator layer;
the scintillator support layer comprises:
a substantially non-planar surface;
a test surface opposite and approximately parallel to the substantially non-planar surface; and
a scintillator support layer thickness greater than approximately 200 micrometers and less than or equal to approximately 300 micrometers;
the scintillator layer comprises:
a first surface;
a second surface opposite the first surface, the second surface being configured to scintillate; and
one or more granular phosphor materials comprising a diameter of greater than or equal to approximately 2 micrometers and less than or equal to approximately 30 micrometers;
the first surface of the scintillator layer is coupled to the substantially non-planar surface of the scintillator support layer such that the second surface of the scintillator layer comprises a contour of the substantially non-planar surface of the scintillator support layer;
the test surface of the scintillator support layer complements the contour of the substantially non-planar surface of the scintillator support layer;
the electronic device comprises a device substrate and one or more active sections;
the device substrate comprises a first surface and a second surface opposite the first surface of the device substrate;
the one or more active sections are at the second surface of the device substrate; and
the second surface of the device substrate and the one or more active sections conform to the second surface of the scintillator layer.

12. The imaging system of claim 11, wherein the device substrate comprises a device substrate thickness of less than or equal to approximately 25 micrometers.

13. The imaging system of claim 11, wherein the scintillator layer comprises one or more scintillator layer materials, and the one or more scintillator layer materials comprise terbium doped gadolinium oxysulfide.

14. The imaging system of claim 11, wherein the scintillator support layer comprises one or more scintillator support layer materials, and the one or more scintillator support layer materials comprise at least one thermoplastic polymer.

15. The imaging system of claim 11, wherein the scintillator layer comprises a scintillator layer thickness greater than or equal to approximately 50 micrometers and less than or equal to approximately 150 micrometers.

16. The imaging system of claim 11, wherein:
each respective active section of the one or more active sections comprises at least one respective semiconductor device; and
each respective semiconductor device of the at least one respective semiconductor device comprises at least one respective detector pixel.

17. The imaging system of claim 11, wherein the electronic device is coupled to the scintillator structure.

18. The imaging system of claim 11, wherein the substantially non-planar surface comprises a non-planar manifold.

19. The imaging system of claim 11, wherein the scintillator layer is located over the scintillator support layer.

20. The imaging system of claim 11, wherein the device substrate further comprises a flexible substrate.

* * * * *